US007803386B2

(12) United States Patent
Schneerson et al.

(10) Patent No.: US 7,803,386 B2
(45) Date of Patent: Sep. 28, 2010

(54) POLY-GAMMA-GLUTAMIC CONJUGATES FOR ELICITING IMMUNE RESPONSES DIRECTED AGAINST BACILLI

(75) Inventors: Rachel Schneerson, Bethesda, MD (US); Stephen Leppla, Bethesda, MD (US); John B. Robbins, Chevy Chase, MD (US); Joseph Shiloach, Rockville, MD (US); Joanna Kubler-Kielb, Rockville, MD (US); Darrell Liu, Bethesda, MD (US); Fathy Majadly, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/559,825

(22) PCT Filed: Jun. 4, 2004

(86) PCT No.: PCT/US2004/017736

§ 371 (c)(1),
(2), (4) Date: Dec. 2, 2005

(87) PCT Pub. No.: WO2005/000884

PCT Pub. Date: Jan. 6, 2005

(65) Prior Publication Data

US 2006/0134143 A1 Jun. 22, 2006

Related U.S. Application Data

(60) Provisional application No. 60/476,598, filed on Jun. 5, 2003.

(51) Int. Cl.
*A61K 39/02* (2006.01)
*A61K 49/00* (2006.01)
*A61K 39/07* (2006.01)

(52) U.S. Cl. .................. 424/234.1; 424/9.1; 424/9.2; 424/184.1; 424/192.1; 424/193.1; 424/197.11; 424/203.1; 424/246.1; 424/278.1

(58) Field of Classification Search .................. 424/9.1, 424/9.2, 184.1, 192.1, 193.1, 197.11, 203.1, 424/234.1, 246.1, 278.1
See application file for complete search history.

(56) References Cited

U.S. PATENT DOCUMENTS

| 4,496,538 A | 1/1985 | Gordon et al. |
| 5,521,290 A | 5/1996 | Sivam et al. |
| 2005/0271675 A1 | 12/2005 | Schneerson et al. |

FOREIGN PATENT DOCUMENTS

WO WO 01/60412 A2 8/2001

WO WO 02/057422 A2 7/2002
WO WO 2005/117965 A1 12/2005

OTHER PUBLICATIONS

Welkos, S., et al, Microbiology, vol. 147, pp. 1677-1685, 2001.*
Pozsgay, V., et al. Proc. Natl. Acad. Sci., USA, vol. 96, pp. 5194-5197, 1999.*
Alkan, S.S. et al. J. of Immunology, vol. 107, No. 2, pp. 353-358, 1971.*
Heitzmann et al., "Use of the Avidin-Biotin Complex for Specific Staining of Biological Membranes in Electron Microscopy," *Proc. Nat. Acad. Sci. USA* 71(9):3537-3541, 1974.
Itaya et al., "Cell Surface Labeling of Erythrocyte Glycoproteins by Galactose Oxidase and $Mn^{++}$-Catalyzed Coupling Reaction with Methionine Sulfone Hydrazide," *Biochemical and Biophysical Research Communications* 64(3):1028-1035, 1975.
Kozel et al., "mAbs to Bacillus anthracis capsular antigen for immunoprotection in anthrax and detection of antigenemia," *PNAS* 101(14):5042-5047, 2004.
Kubler-Kielb et al., "Chemical Structure, Conjugation, and Cross-Reactivity of Bacillus pumilus Sh18 Cell Wall Polysaccharide," *Journal of Bacteriology* 186(20):6891-6901, 2004.
Kubler-Kielb et al., "Additional Conjugation Methods and Immunogenicity of Bacillus anthracis Poly-γ-D-Glutamic Acid-Protein Conjugates," *Infection and Immunity* 74(8):4744-4749, 2006.
Rando et al., "Threshold Effects on the Concavavalin A-mediated Agglutination of Modified Erythrocytes," *The Journal of Biological Chemistry* 254(17):8318-8323, 1979.
Alkan et al., "Antigen recognition and the immune response: The Capacity of L-tyrosine-azobenzenearsonate to serve as a carrier for a macromolecular hapten," *Journal of Immunology* 107(2):353-358, 1971.
Devi et al., "*Cryptococcus-neoformans* Serotype A Glucuronoxylomannan-Protein Conjugate Vaccines: Synthesis, Characterization and Immunogenicity," *Infection and Immunity* 59(10):3700-3707, 1991.
Emmanuel et al., "Poly-gamma-D-glutamic acid as a template for functionalized water-soluble biomaterials," *Abstracts of Papers American Chemical Society* 219(1-2):BIOL 133, 2000, and 219th Meeting of the American Chemical Society, San Francisco, California, Mar. 26-30, 2000.
Goodman et al., "Immunochemical Studies on the Poly-gamma-D-glutamyl Capsule of Bacillus anthracis. 3. The Activity with Rabbit Antisera of Peptides Derived from the Homologous Polypeptide" *Biochemistry* 7(2):706-710, 1968.
King et al., "Preparation of Protein Conjugates via Intermolecular Hydrazone Linkage," *Biochemistry* 25:5774-5779, 1986.

(Continued)

*Primary Examiner*—Rodney P. Swartz
(74) *Attorney, Agent, or Firm*—Klarquist Sparkman, LLP

(57) ABSTRACT

Immunogenic compositions and methods for eliciting an immune response against *B. anthracis* and other bacilli are provided that include immunogenic conjugates of a poly-γ-glutamic acid (γPGA) polypeptide of *B. anthracis*, or of another *Bacillus* that expresses a γPGA polypeptide. The γPGA conjugates elicit an effective immune response against *B. anthracis*, or against another *Bacillus*, in mammalian hosts to which the conjugates are administered.

42 Claims, 2 Drawing Sheets

OTHER PUBLICATIONS

Klaus et al., "The immunological properties of haptens coupled to thymus-independent carrier molecules: III. The role of the immunogenicity and mitogenicity of the carrier in the induction of primary IgM anti-hapten responses," *European Journal of Immunology* 5(2):105-111, 1975.

Leppla et al., "Development of an improved vaccine for anthrax," *Journal of Clinical Investigation* 110(2):141-144, 2002.

Pannifer et al., "Crystal structure of the anthrax legal factor," *Nature* 414:229-233, 2001.

Pozsgay et al., "Protein conjugates of synthetic saccharides elicit higher levels of serum IgG lipopolysaccharide antibodies in mice than do those of the O-specific polysaccharide from *Shigella dysenteriae* type 1," *Proc. Natl. Acad. Sci. USA* 96:5194-5197, 1999.

Ramirez et al., "Production, recovery and immunogenicity of the protective antigen from a recombinant strain of *Bacillus anthracis,*" *Journal of Industrial Microbiology and Biotechnology* 28:232-238, 2002.
Rhie et al., "A dually active anthrax vaccine that confers protection against both Bacilli and toxins," *PNAS* 100(19):10925-10930, 2003.
Robbins et al., "Prevention of Systemic Infections, Especially Meningitis, Caused by *Haemophilus influenzae* Type b," *JAMA* 276(14):1181-1185, 1996.
Schneerson et al., "Preparation, Characterization, and Immunogenicity of *Haemophilus Influenzae* Type b Polysaccharide-protein Conjugates," *Journal of Experimental Medicine* 152(2):361-376, 1980.
Schneerson et al., "Poly(gamma-D-glutamic acid) protein conjugates induce IgG antibodies in mice to the capsule of Bacillus anthracis: A potential addition to the anthrax vaccine," *PNAS* 100(15):8945-8950, 2003.
Senyk et al., "Immune response to glucagons in conjugated form," *Immunochemistry* 9(2):97-110, 1972.
Shinefield et al., "Use of a *Staphylococcus Aureus* Conjugate Vaccine in Patients Receiving Hemodialysis," *The New England Journal of Medicine* 346:491-496, 2002.
Welkos et al., "The role of antibodies to *Bacillus anthracis* and anthrax toxin components in inhibiting the early stages of infection by anthrax spores," *Microbiology* 147(6):1677-1685, 2001.
Ying et al., "The Efficacy of a *Salmonella Typhi* Vi Conjugate vaccine in two-to-five-year-old children," *The New England Journal of Medicine* 344:1263-1269, 2001.
International Search Report, International Application No. PCT/US2004/017736, dated Jun. 5, 2003.
International Search Report, International Application No. PCT/US2005/019678, dated Oct. 12, 2005.
Sep. 21, 2006 Office action from U.S. Appl. No. 11/005,851.
May 17, 2007 Office action from U.S. Appl. No. 11/005,851.
Mar. 3, 2008 Office action from U.S. Appl. No. 11/005,851.
Office action dated Nov. 13, 2008 in U.S. Appl. No. 11/005,851.

* cited by examiner

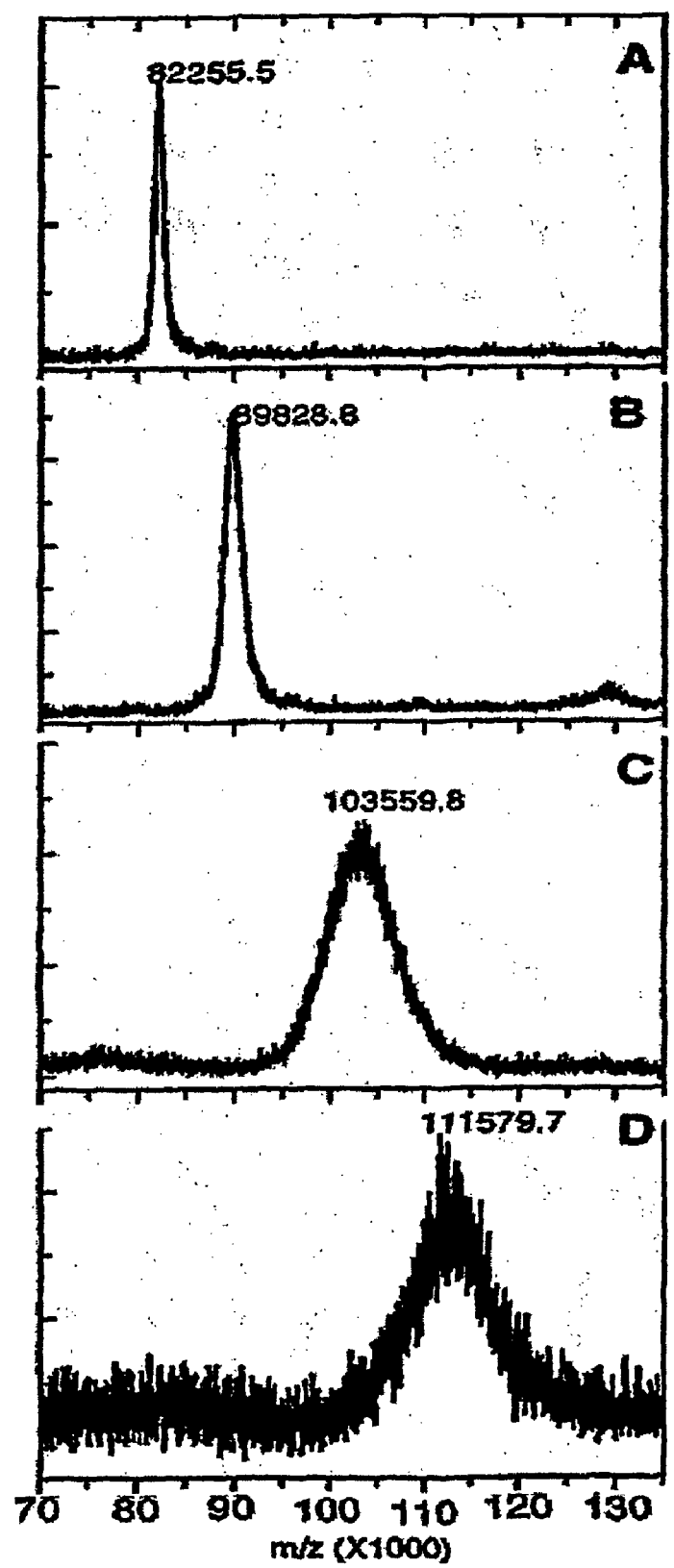
FIG. 2A-D

SEQUENCE LISTING

<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Basic peptide derived from HIV-1 Tat protein.

<400> SEQUENCE: 1

Gly Arg Lys Lys Arg Arg Gln Arg Arg Arg Pro Pro Gln
1               5                   10

<210> SEQ ID NO 2
<211> LENGTH: 2295
<212> TYPE: DNA
<213> ORGANISM: Bacillus anthracis
<220> FEATURE:
<221> NAME/KEY: CDS
<222> LOCATION: (1)..(2292)

<400> SEQUENCE: 2 atg aaa aaa cga aaa gtg tta ata cca tta atg gca ttg tct acg ata       48
Met Lys Lys Arg Lys Val Leu Ile Pro Leu Met Ala Leu Ser Thr Ile
1               5                   10                  15 tta gtt tca agc aca ggt aat tta gag gtg att cag gca gaa gtt aaa       96
Leu Val Ser Ser Thr Gly Asn Leu Glu Val Ile Gln Ala Glu Val Lys
            20                  25                  30 cag gag aac cgg tta tta aat gaa tca gaa tca agt tcc cag ggg tta      144
Gln Glu Asn Arg Leu Leu Asn Glu Ser Glu Ser Ser Ser Gln Gly Leu
        35                  40                  45 cta gga tac tat ttt agt gat ttg aat ttt caa gca ccc atg gtg gtt      192
Leu Gly Tyr Tyr Phe Ser Asp Leu Asn Phe Gln Ala Pro Met Val Val
    50                  55                  60 acc tct tct act aca ggg gat tta tct att cct agt tct gag tta gaa      240
Thr Ser Ser Thr Thr Gly Asp Leu Ser Ile Pro Ser Ser Glu Leu Glu
65                  70                  75                  80 aat att cca tcg gaa aac caa tat ttt caa tct gct att tgg tca gga      288
Asn Ile Pro Ser Glu Asn Gln Tyr Phe Gln Ser Ala Ile Trp Ser Gly
                85                  90                  95 ttt atc aaa gtt aag aag agt gat gaa tat aca ttt gct act tcc gct      336
Phe Ile Lys Val Lys Lys Ser Asp Glu Tyr Thr Phe Ala Thr Ser Ala
            100                 105                 110 gat aat cat gta aca atg tgg gta gat gac caa gaa gtg att aat aaa      384
Asp Asn His Val Thr Met Trp Val Asp Asp Gln Glu Val Ile Asn Lys
        115                 120                 125 gct tct aat tct aac aaa atc aga tta gaa aaa gga aga tta tat caa      432
Ala Ser Asn Ser Asn Lys Ile Arg Leu Glu Lys Gly Arg Leu Tyr Gln
    130                 135                 140 ata aaa att caa tat caa cga gaa aat cct act gaa aaa gga ttg gat      480
Ile Lys Ile Gln Tyr Gln Arg Glu Asn Pro Thr Glu Lys Gly Leu Asp
145                 150                 155                 160 ttc aag ttg tac tgg acc gat tct caa aat aaa aaa gaa gtg att tct      528
Phe Lys Leu Tyr Trp Thr Asp Ser Gln Asn Lys Lys Glu Val Ile Ser
                165                 170                 175 agt gat aac tta caa ttg cca gaa tta aaa caa aaa tct tcg aac tca      576
Ser Asp Asn Leu Gln Leu Pro Glu Leu Lys Gln Lys Ser Ser Asn Ser
            180                 185                 190 aga aaa aag cga agt aca agt gct gga cct acg gtt cca gac cgt gac      624
Arg Lys Lys Arg Ser Thr Ser Ala Gly Pro Thr Val Pro Asp Arg Asp
        195                 200                 205

-continued

| | | |
|---|---|---|
| aat gat gga atc cct gat tca tta gag gta gaa gga tat acg gtt gat<br>Asn Asp Gly Ile Pro Asp Ser Leu Glu Val Glu Gly Tyr Thr Val Asp<br>210                        215                    220 | 672 |
| gtc aaa aat aaa aga act ttt ctt tca cca tgg att tct aat att cat<br>Val Lys Asn Lys Arg Thr Phe Leu Ser Pro Trp Ile Ser Asn Ile His<br>225                    230                    235                  240 | 720 |
| gaa aag aaa gga tta acc aaa tat aaa tca tct cct gaa aaa tgg agc<br>Glu Lys Lys Gly Leu Thr Lys Tyr Lys Ser Ser Pro Glu Lys Trp Ser<br>                    245                    250                  255 | 768 |
| acg gct tct gat ccg tac agt gat ttc gaa aag gtt aca gga cgg att<br>Thr Ala Ser Asp Pro Tyr Ser Asp Phe Glu Lys Val Thr Gly Arg Ile<br>                260                    265                  270 | 816 |
| gat aag aat gta tca cca gag gca aga cac ccc ctt gtg gca gct tat<br>Asp Lys Asn Val Ser Pro Glu Ala Arg His Pro Leu Val Ala Ala Tyr<br>                275                    280                  285 | 864 |
| ccg att gta cat gta gat atg gag aat att att ctc tca aaa aat gag<br>Pro Ile Val His Val Asp Met Glu Asn Ile Ile Leu Ser Lys Asn Glu<br>                290                    295                  300 | 912 |
| gat caa tcc aca cag aat act gat agt caa acg aga aca ata agt aaa<br>Asp Gln Ser Thr Gln Asn Thr Asp Ser Gln Thr Arg Thr Ile Ser Lys<br>305                        310                    315                  320 | 960 |
| aat act tct aca agt agg aca cat act agt gaa gta cat gga aat gca<br>Asn Thr Ser Thr Ser Arg Thr His Thr Ser Glu Val His Gly Asn Ala<br>                    325                    330                  335 | 1008 |
| gaa gtg cat gcg tcg ttc ttt gat att ggt ggg agt gta tct gca gga<br>Glu Val His Ala Ser Phe Phe Asp Ile Gly Gly Ser Val Ser Ala Gly<br>                340                    345                  350 | 1056 |
| ttt agt aat tcg aat tca agt acg gtc gca att gat cat tca cta tct<br>Phe Ser Asn Ser Asn Ser Ser Thr Val Ala Ile Asp His Ser Leu Ser<br>                    355                    360                  365 | 1104 |
| cta gca ggg gaa aga act tgg gct gaa aca atg ggt tta aat acc gct<br>Leu Ala Gly Glu Arg Thr Trp Ala Glu Thr Met Gly Leu Asn Thr Ala<br>              370                    375                  380 | 1152 |
| gat aca gca aga tta aat gcc aat att aga tat gta aat act ggg acg<br>Asp Thr Ala Arg Leu Asn Ala Asn Ile Arg Tyr Val Asn Thr Gly Thr<br>385                        390                    395                  400 | 1200 |
| gct cca atc tac aac gtg tta cca acg act tcg tta gtg tta gga aaa<br>Ala Pro Ile Tyr Asn Val Leu Pro Thr Thr Ser Leu Val Leu Gly Lys<br>                    405                    410                  415 | 1248 |
| aat caa aca ctc gcg aca att aaa gct aag gaa aac caa tta agt caa<br>Asn Gln Thr Leu Ala Thr Ile Lys Ala Lys Glu Asn Gln Leu Ser Gln<br>              420                    425                  430 | 1296 |
| ata ctt gca cct aat aat tat tat cct tct aaa aac ttg gcg cca atc<br>Ile Leu Ala Pro Asn Asn Tyr Tyr Pro Ser Lys Asn Leu Ala Pro Ile<br>              435                    440                  445 | 1344 |
| gca tta aat gca caa gac gat ttc agt tct act cca att aca atg aat<br>Ala Leu Asn Ala Gln Asp Asp Phe Ser Ser Thr Pro Ile Thr Met Asn<br>450                        455                    460 | 1392 |
| tac aat caa ttt ctt gag tta gaa aaa acg aaa caa tta aga tta gat<br>Tyr Asn Gln Phe Leu Glu Leu Glu Lys Thr Lys Gln Leu Arg Leu Asp<br>465                        470                    475                  480 | 1440 |
| acg gat caa gta tat ggg aat ata gca aca tac aat ttt gaa aat gga<br>Thr Asp Gln Val Tyr Gly Asn Ile Ala Thr Tyr Asn Phe Glu Asn Gly<br>                    485                    490                  495 | 1488 |
| aga gtg agg gtg gat aca ggc tcg aac tgg agt gaa gtg tta ccg caa<br>Arg Val Arg Val Asp Thr Gly Ser Asn Trp Ser Glu Val Leu Pro Gln<br>                500                    505                  510 | 1536 |
| att caa gaa aca act gca cgt atc att ttt aat gga aaa gat tta aat<br>Ile Gln Glu Thr Thr Ala Arg Ile Ile Phe Asn Gly Lys Asp Leu Asn | 1584 |

-continued

```
                515                 520                 525
ctg gta gaa agg cgg ata gcg gcg gtt aat cct agt gat cca tta gaa    1632
Leu Val Glu Arg Arg Ile Ala Ala Val Asn Pro Ser Asp Pro Leu Glu
    530                 535                 540 acg act aaa ccg gat atg aca tta aaa gaa gcc ctt aaa ata gca ttt    1680
Thr Thr Lys Pro Asp Met Thr Leu Lys Glu Ala Leu Lys Ile Ala Phe
545                 550                 555                 560 gga ttt aac gaa ccg aat gga aac tta caa tat caa ggg aaa gac ata    1728
Gly Phe Asn Glu Pro Asn Gly Asn Leu Gln Tyr Gln Gly Lys Asp Ile
                565                 570                 575 acc gaa ttt gat ttt aat ttc gat caa caa aca tct caa aat atc aag    1776
Thr Glu Phe Asp Phe Asn Phe Asp Gln Gln Thr Ser Gln Asn Ile Lys
            580                 585                 590 aat cag tta gcg gaa tta aac gca act aac ata tat act gta tta gat    1824
Asn Gln Leu Ala Glu Leu Asn Ala Thr Asn Ile Tyr Thr Val Leu Asp
        595                 600                 605 aaa atc aaa tta aat gca aaa atg aat att tta ata aga gat aaa cgt    1872
Lys Ile Lys Leu Asn Ala Lys Met Asn Ile Leu Ile Arg Asp Lys Arg
    610                 615                 620 ttt cat tat gat aga aat aac ata gca gtt ggg gcg gat gag tca gta    1920
Phe His Tyr Asp Arg Asn Asn Ile Ala Val Gly Ala Asp Glu Ser Val
625                 630                 635                 640 gtt aag gag gct cat aga gaa gta att aat tcg tca aca gag gga tta    1968
Val Lys Glu Ala His Arg Glu Val Ile Asn Ser Ser Thr Glu Gly Leu
                645                 650                 655 ttg tta aat att gat aag gat ata aga aaa ata tta tca ggt tat att    2016
Leu Leu Asn Ile Asp Lys Asp Ile Arg Lys Ile Leu Ser Gly Tyr Ile
            660                 665                 670 gta gaa att gaa gat act gaa ggg ctt aaa gaa gtt ata aat gac aga    2064
Val Glu Ile Glu Asp Thr Glu Gly Leu Lys Glu Val Ile Asn Asp Arg
        675                 680                 685 tat gat atg ttg aat att tct agt tta cgg caa gat gga aaa aca ttt    2112
Tyr Asp Met Leu Asn Ile Ser Ser Leu Arg Gln Asp Gly Lys Thr Phe
    690                 695                 700 ata gat ttt aaa aaa tat aat gat aaa tta ccg tta tat ata agt aat    2160
Ile Asp Phe Lys Lys Tyr Asn Asp Lys Leu Pro Leu Tyr Ile Ser Asn
705                 710                 715                 720 ccc aat tat aag gta aat gta tat gct gtt act aaa gaa aac act att    2208
Pro Asn Tyr Lys Val Asn Val Tyr Ala Val Thr Lys Glu Asn Thr Ile
                725                 730                 735 att aat cct agt gag aat ggg gat act agt acc aac ggg atc aag aaa    2256
Ile Asn Pro Ser Glu Asn Gly Asp Thr Ser Thr Asn Gly Ile Lys Lys
            740                 745                 750 att tta atc ttt tct aaa aaa ggc tat gag ata gga taa                2295
Ile Leu Ile Phe Ser Lys Lys Gly Tyr Glu Ile Gly
        755                 760

<210> SEQ ID NO 3
<211> LENGTH: 764
<212> TYPE: PRT
<213> ORGANISM: Bacillus anthracis

<400> SEQUENCE: 3

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
                20                  25                  30

Gln Glu Asn Arg Leu Leu Asn Glu Ser Glu Ser Ser Gln Gly Leu
        35                  40                  45
```

-continued

```
Leu Gly Tyr Tyr Phe Ser Asp Leu Asn Phe Gln Ala Pro Met Val Val
 50                  55                  60

Thr Ser Ser Thr Thr Gly Asp Leu Ser Ile Pro Ser Ser Glu Leu Glu
 65                      70                  75                  80

Asn Ile Pro Ser Glu Asn Gln Tyr Phe Gln Ser Ala Ile Trp Ser Gly
                     85                  90                  95

Phe Ile Lys Val Lys Lys Ser Asp Glu Tyr Thr Phe Ala Thr Ser Ala
                100                 105                 110

Asp Asn His Val Thr Met Trp Val Asp Gln Glu Val Ile Asn Lys
                115                 120                 125

Ala Ser Asn Ser Asn Lys Ile Arg Leu Glu Lys Gly Arg Leu Tyr Gln
130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
                180                 185                 190

Arg Lys Lys Arg Ser Thr Ser Ala Gly Pro Thr Val Pro Asp Arg Asp
                195                 200                 205

Asn Asp Gly Ile Pro Asp Ser Leu Glu Val Glu Gly Tyr Thr Val Asp
210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
                260                 265                 270

Asp Lys Asn Val Ser Pro Glu Ala Arg His Pro Leu Val Ala Ala Tyr
                275                 280                 285

Pro Ile Val His Val Asp Met Glu Asn Ile Ile Leu Ser Lys Asn Glu
                290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
                340                 345                 350

Phe Ser Asn Ser Asn Ser Ser Thr Val Ala Ile Asp His Ser Leu Ser
                355                 360                 365

Leu Ala Gly Glu Arg Thr Trp Ala Glu Thr Met Gly Leu Asn Thr Ala
                370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
                420                 425                 430

Ile Leu Ala Pro Asn Asn Tyr Tyr Pro Ser Lys Asn Leu Ala Pro Ile
                435                 440                 445

Ala Leu Asn Ala Gln Asp Asp Phe Ser Ser Thr Pro Ile Thr Met Asn
450                 455                 460

Tyr Asn Gln Phe Leu Glu Leu Glu Lys Thr Lys Gln Leu Arg Leu Asp
```

-continued

```
465                 470                 475                 480
Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
                500                 505                 510

Ile Gln Glu Thr Thr Ala Arg Ile Ile Phe Asn Gly Lys Asp Leu Asn
                515                 520                 525

Leu Val Glu Arg Arg Ile Ala Ala Val Asn Pro Ser Asp Pro Leu Glu
        530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
                580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
        610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
                660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
        690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
                740                 745                 750

Ile Leu Ile Phe Ser Lys Lys Gly Tyr Glu Ile Gly
        755                 760
```

POLY-GAMMA-GLUTAMIC CONJUGATES FOR ELICITING IMMUNE RESPONSES DIRECTED AGAINST BACILLI

PRIORITY CLAIM

This is the §371 U.S. National Stage of International Application No. PCT/US2004/017736, filed Jun. 4, 2004, which was published in English under PCT Article 21(2), which in turn claims the benefit of U.S. Provisional Patent Application No. 60/476,598, filed Jun. 5, 2003, which is incorporated herein by reference in its entirety.

FIELD OF THE DISCLOSURE

This invention relates to the field of immunology and, more specifically, to immunogenic compositions and methods for eliciting an effective immune response against *Bacillus anthracis* (.*anthracis*).

BACKGROUND

Anthrax is an acute infectious disease caused by the bacterium *B. anthracis*. Anthrax mc commonly occurs in wild and domestic lower vertebrates (cattle, sheep, goats, camels, antelopes, other herbivores), but it can also occur in humans, for example, when they are exposed to infected animals or tissue from infected animals, or anthrax spores.

The virulence of *B. anthracis* is dependent on Anthrax Toxin (AT), and the poly-γ-D-glutamic acid capsule (γD-PGA). The genes for the toxin, and the capsule, are carried by plasmids designated pX01 and pX02, respectively (Mikesell et al, *Infect. Immun.* 39:371-76, 1983; Vodkin al., *Cell* 34:693-97, 1983; Green et al., *Infect. Immun.* 49:291-97, 1985). AT is composed of three entities: Protective Antigen (PA) (the binding subunit of AT), and two enzymes known as Lethal Factor (LF) and Edema Factor (EF) (Mikesell et al., *Infect. Immun.* 39:371-76, 1983; Vodkin et al *Cell* 34:693-97, 1983). PA is an 83 kDa protein that is the main protective constituent of anthrax vaccines.

PA is necessary for vaccine immunogenicity (Ivins et al., *Infect. Immun.* 60:662-68, 1992; Welkos and Friedlander, *Microb. Pathog.* 5:127, 1998). Antibodies against PA prevent anthrax toxin from binding to host cells, thus abrogating toxicity (Little and Ivins, *Microbes. Infect.* 1:131-39, 1999). Additionally, antibodies to PA can inhibit the germination of spores while improving their phagocytosis and killing by macrophages (Welkos eta., *Microbiology* 147:1677-85, 2001). Unfortunately, the currently licensed human anthrax vaccine (AVA, BioPort Corporation, Lansing Mich.) requires six vaccinations over eighteen months followed by yearly boosters to induce and maintain protective anti-PA titers (Pittman et al., *Vaccine* 20:1412-20, 2002; Pittman et al., *Vaccine* 20:972-78, 2001). In some vaccines, this regimen is associated with undesirable local reactogenic (Pittman et al., *Vaccine* 20:972-78, 2001).

Thus, while certain prophylactic and treatment schemes may prove useful in preventing o directed toward anthrax. In particular, there is a need for an effective and safe vaccine that would require fewer doses to confer immunity to anthrax.

BRIEF SUMMARY OF SPECIFIC EMBODIMENTS

An immunogenic conjugate is disclosed herein The immunogenic conjugate includes a *Bacillus* capsular poly-γ-glutamic acid (γPGA) polypeptide covalently linked to a carrier, wherein the conjugate elicits an immune response in a subject. A composition including the immunogenic conjugate and a pharmaceutically acceptable carrier is also disclosed herein.

A method of eliciting an immune response against a *Bacillus* antigenic epitope in a subject is also disclosed. The method includes introducing into the subject a composition including the immunogenic conjugate and a pharmaceutically acceptable carrier, thereby eliciting an immune response in the subject. Optionally, the composition includes an adjuvant.

Further disclosed herein are isolated antibodies that bind to the *Bacillus* γPGA polypeptide. In one embodiment, the isolated antibodies recognize antigenic epitopes on both the *Bacillus* γPGA polypeptide and the carrier protein.

BRIEF DESCRIPTION OF THE FIGURES

FIG. 2A-2D are a set of MALDI-TOF spectra, showing the mass spectra of recombinant *B. anthracis* rPA (FIG. 2A); Br-rPA (FIG. 2B); rPA-Cys-Gly$_3$-γDPGA$_{10}$-C conjugate containing an average of 11 γDPGA chains per rPA (FIG. 2C); and rPA-Cys-Gly$_3$-γDPGA$_{10}$-C conjugate containing an average of 16 γDPGA chains per rPA (FIG. 2D).

SEQUENCE LISTING

Figure 1:
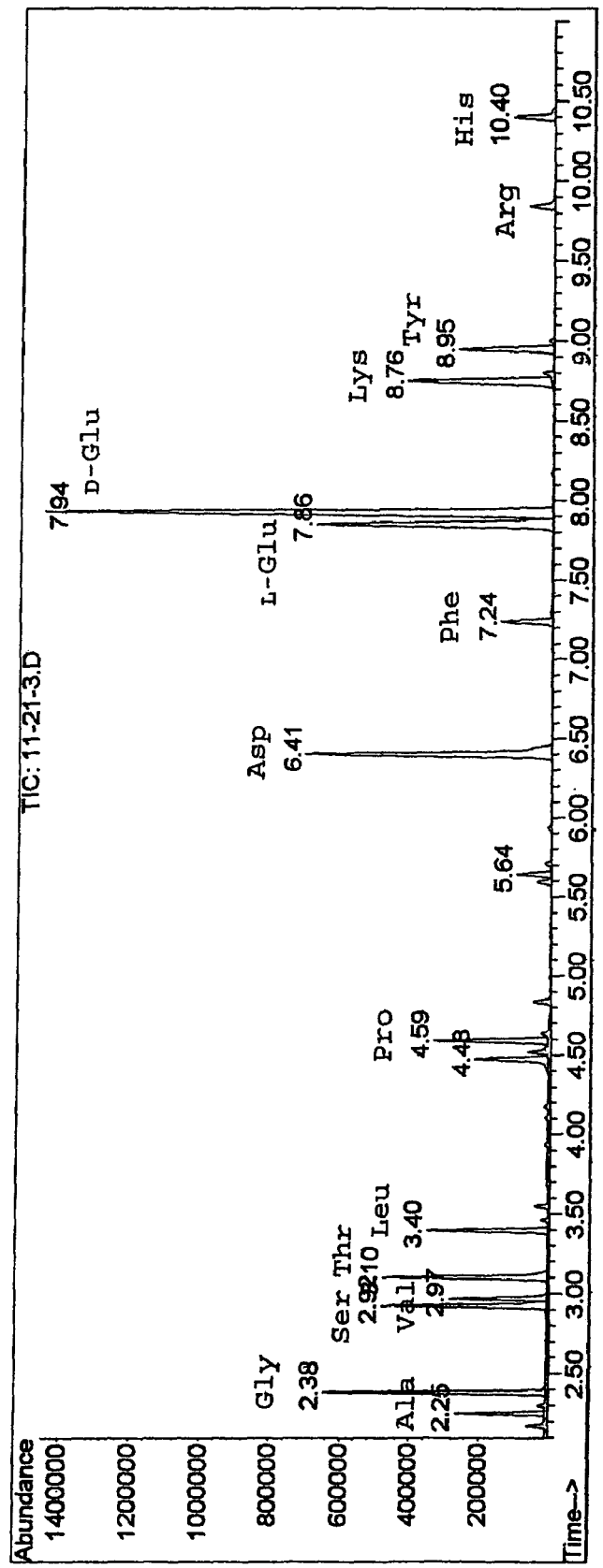
FIG. 1 is a GLC-MS spectrum analysis of the rPA-Cys-Gly$_3$-γDPGA$_{10}$-C conjugate, demonstrating that L-Glu can be separated from D-Glu and measured in order to calculate the number of γDPGA chains incorporated into the protein of the conjugate.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the amino acid sequence of human immunodeficiency virus (HIV)-1 Tat protein.

SEQ ID NOs: 2 and 3 show the nucleic and amino acid sequences of *B. anthracis* protective antigen.

DETAILED DESCRIPTION OF SEVERAL EMBODIMENTS

I. Abbreviations

| | |
|---|---|
| ADH: | adipic acid dihydrazide |
| AT: | anthrax toxin |
| ATR: | anthrax toxin receptor |
| EDAC: | 1-ethyl-3-(3-dimethylaminopropyl)carbodiimide-HCl |
| EF: | edema factor |
| γPGA: | poly-γ-glutamic acid capsule from a *Bacillus* |
| γDPGA: | poly-γ-D- glutamic acid capsule from *B. anthracis* |
| γLPGA: | poly-γ-L- glutamic acid capsule from a *Bacillus* |
| GLC-MS: | gas-liquid chromatography-mass spectrometry |
| kDa: | kilodaltons |
| LC-MS: | liquid chromatography-mass spectrometry |
| LeTx: | lethal toxin |
| LF: | lethal factor |
| LPS: | lipopolysaccharide |
| MALDI-TOF: | matrix-assisted laser desorption ionization time-of-flight |
| μg: | microgram |
| μl: | microliter |
| PA: | protective antigen |

-continued

| PBS: | phosphate buffered saline |
| --- | --- |
| rEPA: | recombinant *Pseudomonas aeruginosa* exotoxin A |
| rPA: | recombinant *B. anthracis* protective antigen |
| SBAP: | succinimidyl 3-(bromoacetamido) propionate |
| SFB: | succinimidylformylbenzoate |
| SPDP: | N-hydroxysuccinimide ester of 3-(2-pyridyl dithio)-propionic acid |
| SLV: | succinimidyllevulinate |

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Adjuvant: A substance that non-specifically enhances the immune response to an antigen. Development of vaccine adjuvants for use in humans is reviewed in Singh et al. (*Nat. Biotechnol.* 17:1075-1081, 1999), which discloses that, at the time of its publication, aluminum salts, such as aluminum hydroxide (Amphogel, Wyeth Laboratories, Madison, N.J.), and the MF59 microemulsion are the only vaccine adjuvants approved for human use.

In one embodiment, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CpG oligodeoxynucleotides, as described in U.S. Pat. Nos. 6,194,388; 6,207,646; 6,214,806; 6,218,371; 6,239,116; 6,339,068; 6,406,705; and 6,429,199.

Analog, Derivative or Mimetic: An analog is a molecule that differs in chemical structure from a parent compound, for example a homolog (differing by an increment in the chemical structure, such as a difference in the length of an allyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that may be specifically bound by the products of specific humoral or cellular immunity, such as an antibody molecule or T-cell receptor. In one embodiment, an antigen is a *Bacillus* antigen, such as γPGA.

*Bacillus*: A genus of bacteria whose collective features include degradation of most substrates derived from plant and animal sources, including cellulose, starch, pectin, proteins, agar, hydrocarbons, and others; antibiotic production; nitrification; denitrification; nitrogen fixation; facultative lithotrophy; autotrophy; acidophily; alkaliphily; psychrophily, thermophily and parasitism. Spore formation, universally found in the genus, is thought to be a strategy for survival in the soil environment, wherein the bacteria predominate. Aerial distribution of dormant spores likely explains the occurrence of *Bacillus* species in most habitats examined.

There are more than 40 recognized species in the genus *Bacillus* (Bergey's Manual of Systematic Bacteriology Vol. 2 (1986)). These include, but are not limited to, *B. acidocaldarius, B. alkalophilus, B. alvei, B. anthracis, B. azotoformans, B. badius, B. brevis, B. cereus, B. circulans, B. coagulans, B. fastidiosis, B. firmus, B. globisporus, B. insolitus, B. larvae, B. laterosporus, B. lentinorbus, B. lentus, B. licheniformis, B. macerans, B. macquariensis, B. marinus, B. megaterium, B. mycoides, B. pantothenticus, B. pasteurii, B. polymyxa, B. popillia, B. pumilus, B. schlegelii, B. sphaericus, B. stearothermophilus, B. subtilis,* and *B. thuringiensis*. In one specific, non-limiting example, a *Bacillus* is *Bacillus anthracis*, the agent that causes anthrax.

*Bacillus Anthracis*: The etiologic agent of anthrax, *Bacillus anthracis* is a large, gram-positive, nonmotile, spore-forming bacterial rod. The virulence of *B. anthracis* is dependent on AT, and the γDPGA capsule. The genes for the toxin, and the capsule, are carried by plasmids, designated pX01 and pX02, respectively (Mikesell et al., *Infect Immune*. 39:371-76, 1983; Vodkin et al., *Cell* 34:693-97, 1983; Green et al., *Infect Immun.* 49:291-97, 1985).

AT is composed of three entities: PA (the binding subunit of AT), and two enzymes known as LF and EF (Mikesell et al., *Infect. Immun.* 39:371-76, 1983; Vodkin et al., *Cell* 34:693-97, 1983). PA is an 83 kDa protein that is the main protective constituent of anthrax vaccines. PA binds to the anthrax toxin receptor (ATR) on cells and is then proteolytically cleaved by the enzyme furin with release of a 20 kDa fragment (Bradley et al., *Nature* 414:225-29, 2001; Klimpel et al., *PNAS* 89:10277-81, 1992). The 63 kDa PA remnant ($PA_{63}$) features a second binding domain and binds to either EF, an 89 kDa protein, to form edema toxin, or LF, a 90 kDa protein, to form lethal toxin (LeTx) (Leppla et al., *Salisbury Med. Bull. Suppl.* 68:41-43, 1990). The resulting complex is internalized into the cell within endosomes (Singh et al, *Infect. Immun.* 67:1853-59, 1999; Friedlander, *J. Biol. Chem.* 261:7123-26, 1986).

The γDPGA capsule of *B. anthracis* serves as an essential virulence factor during anthrax infection, inhibiting host defense mechanisms through inhibition of phagocytosis of the vegetative cells by macrophages. While other *Bacillus* produce γPGA in a mixture of both D- and L-forms, only *B. anthracis* is known to synthesize it exclusively in a D-conformation (Kovács et al., *J. Chem. Soc.* 4255-59, 1952). When injected, γDPGA has been shown to be a poor immunogen (Eisner, *Schweiz. Z. Pathol. Bakteriol.* 22:129-44, 1959; Ostroff et al., *Proc. Soc. Exp. Biol. Med.* 99:345-47, 1958). The capsule also shields the vegetative form of *B. anthracis* from agglutination by monoclonal antibodies to its cell wall polysaccharide (Ezzell et al., *J. Clin. Microbiol.* 28:223-31, 1990).

Carrier: An immunogenic macromolecule to which an antigenic but not highly immunogenic molecule, such as, for example, a homopolymer of γPGA, can be bound. When bound to a carrier, the bound molecule becomes more immunogenic. Carriers are chosen to increase the immunogenicity of the bound molecule and/or to elicit antibodies against the carrier which are diagnostically, analytically, and/or therapeutically beneficial. Covalent linking of a molecule to a carrier confers enhanced immunogenicity and T-cell dependence (Pozsgay et al., *PNAS* 96:5194-97, 1999; Lee et al, *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached.

Examples of bacterial products for use as carriers include bacterial toxins, such as *B. anthracis* PA (including fragments that contain at least one antigenic epitope and analogs or derivatives capable of eliciting an immune response), LF and LeTx, and other bacterial toxins and toxoids, such as tetanus toxin/toxoid, diphtheria toxin/toxoid, *P. aeruginosa* exotoxin/toxoid/, pertussis toxin/toxoid, and *C. perfringens* exotoxin/toxoid. Viral proteins, such as hepatitis B surface antigen and core antigen can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

Covalent Bond: An interatomic bond between two atoms, characterized by the sharing of one or more pairs of electrons by the atoms. The terms "covalently bound" or "covalently linked" refer to making two separate molecules into one contiguous molecule. The terms include reference to joining a γPGA polypeptide directly to a carrier molecule, and to joining a γPGA polypeptide indirectly to a carrier molecule, with an intervening linker molecule.

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

γPGA: A homopolymer of glutamic acid residues linked by γ peptide bonds. The glutamic acid residues constituting the γPGA homopolymer can be solely in the L-form (γLPGA) or the D-form (γDPGA). When the form of the glutamic acid residues constituting the γPGA homopolymer can be either the L-form or the D-form, or when the two forms are mixed in a single molecule, the term γPGA is used. The weakly immunogenic and antiphagocytic capsule found on many species of *Bacillus*, which disguises the bacilli from immune surveillance, consists of γPGA.

γPGA Conjugate: A naturally occurring γPGA polypeptide produced by *B. anthracis* or another *Bacillus* species or strain covalently linked to a carrier, as well as conjugates of a carrier with a polypeptide fragment, synthetic polypeptide, or chemically modified derivative of a γPGA polypeptide. In some embodiments, the γPGA conjugate will comprise a conjugate of a carrier protein with a synthetic γPGA polypeptide having a selected peptide length and corresponding to a portion of a γPGA polypeptide from *B. anthracis* or another *Bacillus* species or strain that possesses a γPGA capsule.

Homopolymer: This term refers to a polymer formed by the bonding together of multiple units of a single type of molecular species, such as a single monomer (for example, an amino acid).

Immune Response: A response of a cell of the immune system, such as a B-cell, T-cell, macrophage or polymorphonucleocyte, to a stimulus. An immune response can include any cell of the body involved in a host defense response for example, an epithelial cell that secretes interferon or a cytokine. An immune response includes, but is not limited to, an innate immune response or inflammation.

Immunogenic Conjugate or Composition: A term used herein to mean a composition useful for stimulating or eliciting a specific immune response (or immunogenic response) in a vertebrate. In some embodiments, the immunogenic response is protective or provides protective immunity, in that it enables the vertebrate animal to better resist infection or disease progression from the organism against which the immunogenic composition is directed.

Without wishing to be bound by a specific theory, it is believed that an immunogenic response can arise from the generation of an antibody specific to one or more of the epitopes provided in the immunogenic composition. The response can include a T-helper or cytotoxic cell-based response to one or more of the epitopes provided in the immunogenic composition. All three of these responses may originate from naïve or memory cells. A response can also include production of cytokines. One specific example of a type of immunogenic composition is a vaccine.

Immunogen: A compound, composition, or substance which is capable, under appropriate conditions, of stimulating the production of antibodies or a T-cell response in an animal, including compositions that are injected or absorbed into an animal.

Immunologically Effective Dose: An immunologically effective dose of the γPGA conjugates of the disclosure is therapeutically effective and will prevent, treat, lessen, or attenuate the severity, extent or duration of a disease or condition, for example, infection by *B. anthracis*.

Inhibiting or Treating a Disease: Inhibiting the fill development of a disease or condition, for example, in a subject who is at risk for a disease such as anthrax. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

Linker: A molecule that joins two other molecules, either covalently, or through ionic, van der Waals or hydrogen bonds.

Opsonin: A macromolecule that becomes attached to the surface of a microbe and can be recognized by surface receptors of neutrophils and macrophages and that increases the efficiency of phagocytosis of the microbe. Opsonins include IgG antibodies, which are recognized by the Fcγ receptor on phagocytes, and fragments of complement proteins, which are recognized by CR1 (CD35) and by the leukocyte integrin Mac-1.

Opsonophagocytosis: The process of attaching opsonins to microbial surfaces to target the microbes for phagocytosis.

PA-based Immunogen: A term used herein to refer to all forms of PA which are useful in immunogenic compositions and/or methods of the disclosure, including unmodified native or recombinant *B. anthracis* PA, or a variant or fragment thereof. Variants and fragments of PA are effective to elicit an anti-PA immune response in a subject to whom they are administered.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more SARS-CoV nucleic acid molecules, proteins or antibodies that bind these proteins, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Protective Antigen (PA): One of the three components of the anthrax toxin. PA is a secreted nontoxic protein with a molecular weight of 83 kDa and is the major protective constituent of anthrax vaccines. PA binds to the ATR on cells and is then proteolytically cleaved by the enzyme furin with release of a 20 kDa fragment (Bradley et al., *Nature* 414:225-29, 2001; Klimpel et al., *PNAS* 89:10277-81, 1992). The 63 kDa PA remnant ($PA_{63}$) features a second binding domain and binds to either EF, an 89 kDa protein, to form edema toxin, or LF, a 90 kDa protein, to form lethal toxin (LeTx). The sequence of PA is known, for example, as encoded by bases 143779 to 146073 of GenBank Accession No. NC 007322 (plasmid pXO1; SEQ ID NOs: 2 and 3, nucleic and amino acid sequences, respectively).

Protein: A biological molecule, particularly a polypeptide, expressed by a gene and comprised of amino acids.

Purified: The term "purified" does not require absolute purity; rather, it is intended as a relative term. Thus, for example, a purified peptide, protein, γPGA conjugate, or other active compound is one that is isolated in whole or in part from naturally associated proteins and other contaminants, wherein the peptide, protein, γPGA conjugate, or other active compound is purified to a measurable degree relative to its naturally occurring state, for example, relative to its purity within a cell extract. In certain embodiments, the term "substantially purified" refers to a peptide, protein, γPGA conjugate, or other active compound that has been isolated from a cell, cell culture medium, or other crude preparation and subjected to fractionation to remove various components of the initial preparation, such as proteins, cellular debris, and other components. Such purified preparations can include materials in covalent association with the active agent, such as glycoside residues or materials admixed or conjugated with the active agent, which may be desired to yield a modified derivative or analog of the active agent or produce a combinatorial therapeutic formulation, conjugate, fusion protein or the like. The term purified thus includes such desired products as peptide and protein analogs or mimetics or other biologically active compounds wherein additional compounds or moieties are bound to the active agent in order to allow for the attachment of other compounds and/or provide for formulations useful in therapeutic treatment or diagnostic procedures. Generally, substantially purified peptides, proteins, γPGA conjugates, or other active compounds for use within the disclosure comprise more than 80% of all macromolecular species present in a preparation prior to admixture or formulation of the peptide, protein, γPGA conjugate or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, γPGA conjugate or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

Recombinant Nucleic Acid: A sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques such as those described in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989. The term recombinant includes nucleic acids that have been altered solely by addition, substitution, or deletion of a portion of the nucleic acid.

Specific Binding Agent: An agent that binds substantially only to a defined target. Thus a protein-specific binding agent binds substantially only the defined protein, or to a specific region within the protein. As used herein, a specific binding agent includes antibodies and other agents that bind substantially to a specified polypeptide. The antibodies may be monoclonal or polyclonal antibodies that are specific for the polypeptide, as well as immunologically effective portions ("fragments") thereof.

The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Spore: A small, usually single-celled reproductive body that is highly resistant to desiccation and heat and is capable of growing into a new organism, produced especially by certain bacteria, fungi, algae, and non-flowering plants. Spores have proven to be the most durable type of cell found in nature, and in their cryptobiotic state of dormancy, they can remain viable for extremely long periods of time, perhaps millions of years. Spores do not form normally during active growth and cell division. Rather, their differentiation begins when a population of vegetative cells passes out of the exponential phase of growth, usually as a result of nutrient depletion. Typically, one spore is formed per vegetative cell. In some examples, the mature spore is liberated by lysis of the mother cell (sporangium) in which it was formed.

Mature spores have no detectable metabolism, a state that is described as cryptobiotic. They are highly resistant to environmental stresses such as high temperature (some spores can be boiled for several hours and retain their viability), irradiation, strong acids, disinfectants, and the like. Although cryptobiotic, they retain viability indefinitely such that under appropriate environmental conditions, they germinate into vegetative cells.

Therapeutically Effective Amount: A quantity of a specified agent sufficient to achieve a desired effect in a subject being treated with that agent. For example, this may be the amount of a γDPGA conjugate useful in increasing resistance to, preventing, ameliorating, and/or treating infection and disease caused by *B. anthracis* infection in a subject Ideally, a therapeutically effective amount of an agent is an amount sufficient to increase resistance to, prevent, ameliorate, and/or treat infection and disease caused by *B. anthracis* infection in a subject without causing a substantial cytotoxic effect in the subject. The effective amount of an agent useful for increasing resistance to, preventing, ameliorating, and/or treating infection and disease caused by *B. anthracis* infection in a subject will be dependent on the subject being treated, the severity of the affliction, and the manner of administration of the therapeutic composition.

Toxoid: A nontoxic derivative of a bacterial exotoxin produced, for example, by formaldehyde or other chemical treatment. Toxoids are useful in the formulation of immunogenic compositions because they retain most of the antigenic properties of the toxins from which they were derived.

III. Description of Several Embodiments

A. *Bacillus* γPGA Polypeptide—Carrier Conjugates

*Bacillus* capsular γPGA polypeptide—carrier conjugates (γPGA conjugates), are disclosed herein. The γPGA conjugates elicit an immune response in a subject, and inhibit or treat infection and/or disease caused by *B. anthracis* or other bacilli.

The weakly immunogenic and antiphagocytic γPGA capsule, which consists of glutamic acid residues linked by γ peptide bonds, disguises the bacilli from immune surveillance. As disclosed herein, *Bacillus* capsular γPGA polypeptides include, but are not limited to, *B. anthracis, B. licheniformis, B. pumilus,* and *B. subtilis* γPGA polypeptides. All *Bacillus* besides *B. anthracis* that are known to produce γPGA make a mixture of both the D- and L-forms, whereas *B. anthracis* produces exclusively γDPGA. In one embodiment, the γPGA conjugates disclosed herein are γLPGA conjugates. In another embodiment, the γPGA conjugates are γDPGA conjugates. In a specific, non-limiting example, the γDPGA conjugate is a *B. anthracis* γDPGA conjugate.

*Bacillus* capsular γPGA polypeptides can be isolated by many methods well known in the art, such as salt fractionation, phenol extraction, precipitation with organic solvents (for example, hexadecyltrimethylammonium bromide (cetavlon) or ethanol), affinity chromatography, ion-exchange chromatography, hydrophobic chromatography, high performance liquid chromatography, gel filtration, isoelectric focusing, and the like. In one specific, non-limiting example, *Bacillus* capsular γPGA polypeptides are extracted from the culture supernatant of growing bacilli by cetavlon precipitation, acidification to pH 1.5, precipitation with ethanol, and passage through a 2.5×100 cm Sepharose CL-4B column in 0.2M NaCl. The compositions of extracted γPGA polypeptides are determined by methods well known in the art, such as $^1$H-nuclear magnetic resonance (NMR) spectroscopy and $^{13}$C-NMR spectroscopy; while their enantiomeric confirmations can be determined by gas-liquid chromatography-mass spectrometry (GLC-MS).

Synthetic γPGA polypeptides of varying lengths (for example, about 5, 10, 15, or 20 residues) having either the D- or L-configuration can be readily synthesized by automated solid phase procedures well known in the art Suitable syntheses can be performed by utilizing "T-boc" or "F-moc" procedures. Techniques and procedures for solid phase synthesis are described in *Solid Phase Peptide Synthesis: A Practical Approach*, by E. Atherton and R. C. Sheppard, published by IRL, Oxford University Press, 1989. In specific, non-limiting examples, the synthetic γPGA polypeptide includes about 1 to about 20 glutamic acid residues, such as about 10 to about 15 glutamic acid residues, or about 10 glutamic acid residues. The compositions and purity of synthetic γPGA polypeptides can be determined by GLC-MS and matrix-assisted laser desorption ionization time-of-flight (MALDI-TOF) spectrometry.

Carriers for linking to γPGA polypeptides as disclosed herein are chosen to increase the immunogenicity of the γPGA polypeptides and/or to elicit antibodies against the carrier which are diagnostically, analytically, and/or therapeutically beneficial. Covalent linking of γPGA polypeptides to a carrier confers enhanced immunogenicity and T-cell dependence. Useful carriers include polymeric carriers, which can be natural, semi-synthetic or synthetic materials containing one or more functional groups, for example primary and/or secondary amino groups, azido groups, hydroxyl groups, or carboxyl groups, to which a reactant moiety can be attached. The carrier can be water soluble or insoluble, and in some embodiments is a protein or polypeptide. Carriers that fulfill these criteria are generally known in the art (see, for example, Fattom et al., *Infect. Immun.* 58:2309-12, 1990; Devi et al., *PNAS* 88:7175-79, 1991; Szu et al., *Infect Immun.* 59:4555-61, 1991; Szu et al., *J. Exp. Med* 166:1510-24, 1987; and Pavliakova et al., *Infect. Immun.* 68:2161-66, 2000).

Specific, non-limiting examples of water soluble polypeptide carriers include, but are not limited to, natural, semi-synthetic or synthetic polypeptides or proteins from bacteria or viruses. In one embodiment, bacterial products for use as carriers include bacterial wall proteins and other products (for example, streptococcal or staphylococcal cell walls and LPS), and soluble antigens of bacteria. In another embodiment, bacterial products for use as carriers include bacterial toxins. Bacterial toxins include bacterial products that mediate toxic effects, inflammatory responses, stress, shock, chronic sequelae, or mortality in a susceptible host. Specific, non-limiting examples of bacterial toxins include, but are not limited to: *B. anthracis* PA (for example, as encoded by bases 143779 to 146073 of GenBank Accession No. NC 007322, herein incorporated by reference), including variants that share at least 90%, at least 95%, or at least 98% amino acid sequence homology to PA, fragments that contain at least one antigenic epitope, and analogs or derivatives capable of eliciting an immune response; *B. anthracis* LF (for example, as encoded by the complement of bases 149357 to 151786 of GenBank Accession No. NC 007322); bacterial toxins and toxoids, such as tetanus toxin/toxoid (for example, as described in U.S. Pat. Nos. 5,601,826 and 6,696,065); diphtheria toxin/toxoid (for example, as described in U.S. Pat.

Nos. 4,709,017 and 6,696,065); *P. aeruginosa* exotoxin/toxoid/(for example, as described in U.S. Pat. Nos. 4,428,931, 4,488,991 and 5,602,095); pertussis toxin/toxoid (for example, as described in U.S. Pat. Nos. 4,997,915, 6,399,076 and 6,696,065); and *C. perfringens* exotoxin/toxoid (for example, as described in U.S. Pat. Nos. 5,817,317 and 6,403, 094). Viral proteins, such as hepatitis B surface antigen (for example, as described in U.S. Pat. Nos. 5,151,023 and 6,013, 264) and core antigen (for example, as described in U.S. Pat. Nos. 4,547,367 and 4,547,368) can also be used as carriers, as well as proteins from higher organisms such as keyhole limpet hemocyanin, horseshoe crab hemocyanin, edestin, mammalian serum albumins, and mammalian immunoglobulins.

In addition to bacterial and viral products, polysaccharide carriers are also useful in preparing the γPGA polypeptide conjugates as disclosed herein. Polysaccharide carriers include, but are not limited to, dextran, capsular polysaccharides from microorganisms such as the Vi capsular polysaccharide from *S. typhi* (see, for example, U.S. Pat. No. 5,204, 098); *Pneumococcus* group 12 (12F and 12A) polysaccharides; *Haemophilus influenazae* type d polysaccharide; and certain plant, fruit, and synthetic oligo- or polysaccharides which are immunologically similar to capsular polysaccharides, such as pectin, D-galacturonan, oligogalacturonate, or polygalacturonate (for example, as described in U.S. Pat. No. 5,738,855).

Specific, non-limiting examples of water insoluble carriers useful in preparing the γPGA polypeptide conjugates as disclosed herein include, but are not limited to, aminoalkyl agarose (for example, aminopropyl or aminohexyl SEPHAROSE; Pharmacia Inc., Piscataway, N.J.), aminopropyl glass, cross-linked dextran, and the like, to which a reactive moiety can be attached. Other carriers can be used, provided that a functional group is available for covalently attaching a reactive group.

Binding of γPGA polypeptides to a carrier can be direct or via a linker element. Linkers can include amino acids, including amino acids capable of forming disulfide bonds, but can also include other molecules such as, for example, polysaccharides or fragments thereof. Linkers can be chosen so as to elicit their own immunogenic effect which nay be either the same, or different, than that elicited by the γPGA polypeptides and/or carriers disclosed herein. For example, such linkers can be bacterial antigens which elicit the production of antibodies to an infectious bacteria. In such instances, for example, the linker can be a protein or protein fragment of an infectious bacterium.

The covalent linking of the γPGA polypeptides disclosed herein to the carrier can be carried out in any manner well known to one of skill in the art. Conjugation methods applicable to the present disclosure include, by way of non-limiting example, reductive amination, diazo coupling, thioether bond, disulfide bond, amidation and thiocarbamoyl chemistries. In one embodiment, the γPGA polypeptides and/or the carrier are "activated" prior to conjugation. Activation provides the necessary chemical groups for the conjugation reaction to occur. In one specific, non-limiting example, the activation step includes derivatization with adipic acid dihydrazide. In another specific, non-limiting example, the activation step includes derivatization with the N-hydroxysuccinimide ester of 3-(2-pyridyl dithio)-propionic acid (SPDP). In yet another specific, non-limiting example, the activation step includes derivatization with succinimidyl 3-(bromoacetamido) propionate (SBAP). Further, non-limiting examples of derivatizing agents include succinimidylformylbenzoate (SFB) and succinimidyllevulinate (SLV).

Following conjugation of a γPGA polypeptide to a carrier, the γPGA polypeptide-carrier conjugate can be purified by a variety of techniques well known to one of skill in the art. One goal of the purification step is to remove the unbound γPGA polypeptide from the γPGA polypeptide-carrier conjugate. One method for purification, involving ultrafiltration in the presence of ammonium sulfate, is described in U.S. Pat. No. 6,146,902. Alternatively, γPGA polypeptide-carrier conjugates can be purified away from unreacted γPGA polypeptide and carrier by any number of standard techniques including, for example, size exclusion chromatography, density gradient centrifugation, hydrophobic interaction chromatography, or ammonium sulfate fractionation. See, for example, Anderson et al., *J. Immunol.* 137:1181-86, 1986 and Jennings & Lugowski, *J. Immunol.* 127:1011-18, 1981. The compositions and purity of the conjugates can be determined by GLC-MS and MALDI-TOF spectrometry.

For γPGA conjugates comprising γPGA polypeptides bound at one point to a carrier, complex structural characteristics determine optimal immunogenicity for synthetic conjugates (see, for example, Kabat, *Prog. Immunol.* 5:67-85, 1983; Pozsgay et al., *PNAS* 96:5194-97, 1999; Lee et al., *J. Immunol.* 116:1711-18, 1976; and Dintzis et al., *PNAS* 73:3671-75, 1976). γPGA polypeptide lengths must be sufficient to occupy a cognate antibody combining site. In addition, the density of the γPGA polypeptide on the carrier determines the ability of the γPGA conjugate to form both aggregates with the surface Ig receptor, and to permit interaction of the carrier fragments with T-cells. In various embodiments of the present disclosure, γPGA conjugates having a density of γPGA polypeptide chains to carrier molecule of between about 5:1 to about 32:1, such as about 8:1 to about 22:1, or about 10:1 to about 15:1, are useful within the immunogenic compositions and methods described herein.

B. Analogs, Derivatives and Mimetics

In additional aspects of the disclosure, a γPGA conjugate, PA-based immunogen, carrier, or component of an immunogenic conjugate or composition of the disclosure, includes a peptide mimetic of a naturally occurring or synthetic agent, for example a γPGA polypeptide derivative of *B. anthracis* or another *Bacillus* species or strain. Exemplary conjugates and compositions are provided which comprise a peptide or non-peptide molecule that mimics the tertiary binding structure and activity of a selected native peptide or functional domain (for example, immunogenic region or epitope) of a γPGA polypeptide, carrier, linker, PA-based immunogen or other component of an immunogenic conjugate or composition of the disclosure. These peptide mimetics include recombinantly or chemically modified peptides, as well as non-peptide agents such as small molecule drug mimetics, as further described herein.

Certain peptidomimetic compounds are based upon the amino acid sequence of the proteins and peptides described herein for use within the disclosure, including sequences of bacterial toxins such as *B. anthracis*. PA (for example, as encoded by bases 143779 to 146073 of GenBank Accession No. NC 007322) and LF (for example, as encoded by the complement of bases 149357 to 151786 of GenBank Accession No. NC 007322). Typically, peptidomimetic compounds are synthetic compounds having a three-dimensional structure (of at least part of the mimetic compound) that mimics, for example, the primary, secondary, and/or tertiary structural, and/or electrochemical characteristics of a selected peptide or protein, or a structural domain, active site, or binding region (for example, a homotypic or heterotypic binding site, catalytic active site or domain, receptor or ligand binding interface or domain) thereof. The peptide-mimetic structure or partial structure (also referred to as a peptidomimetic motif of a peptidomimetic compound) will often share a desired biological activity with a native peptide or protein, as discussed herein (for example, immunogenic activity, such as binding to an antibody or a MHC molecule to activate $CD8^+$ and/or $CD4^+$ T-cells). Typically, at least one subject biological activity of the mimetic compound is not substantially reduced in comparison to, and is often the same as or greater than, the activity of the native peptide on which the mimetic was modeled.

A variety of techniques well known to one of skill in the art are available for constructing peptide and protein mimetics with the same, similar, increased, or reduced biological activity as the corresponding native peptide or protein. Often these analogs, variants, derivatives and mimetics will exhibit one or more desired activities that are distinct or improved from the corresponding native peptide or protein, for example improved characteristics of solubility, stability, and/or susceptibility to hydrolysis or proteolysis (see, for example, Morgan & Gainor, *Ann. Rep. Med. Chem.* 24:243-52, 1989). In addition, peptidomimetic compounds of the disclosure can have other desired characteristics that enhance their therapeutic application, such as increased cell permeability, greater affinity and/or avidity for a binding partner, and/or prolonged biological half-life. The peptidomimetics of the disclosure will sometimes have a backbone that is partially or completely non-peptide, but with side groups identical to the side groups of the amino acid residues that occur in the peptide or protein on which the peptidomimetic is modeled. Several types of chemical bonds, for example, ester, thioester, thioamide, retroamide, reduced carbonyl, dimethylene and ketomethylene bonds, are known in the art to be generally useful substitutes for peptide bonds in the construction of protease-resistant peptidomimetics.

In one embodiment, peptides (including polypeptides) useful within the disclosure are modified to produce peptide mimetics by replacement of one or more naturally occurring side chains of the 20 genetically encoded amino acids (or D-amino acids) with other side chains, for example with groups such as alkyl, lower alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from a 5 membered ring to a 4, 6, or 7 membered ring. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include furazanyl, furyl, imidazolidinyl, imidazolyl, imidazolinyl, isothiazolyl, isoxazolyl, morpholinyl (for example, morpholino), oxazolyl, piperazinyl (for example, 1-piperazinyl), piperidyl (for example, 1-piperidyl, piperidino), pyranyl, pyrazinyl, pyrazolidinyl, pyrazolinyl, pyrazolyl, pyridazinyl, pyridyl, pyrimidinyl, pyrrolidinyl (for example, 1-pyrrolidinyl), pyrrolinyl, pyrrolyl, thiadiazolyl, thiazolyl, thienyl, thiomorpholinyl (for example, thiomorpholino), and triazolyl groups. These heterocyclic groups can be substituted or unsubstituted. Where a group is substituted, the substituent can be alkyl, alkoxy, halogen, oxygen, or substituted or unsubstituted phenyl. Peptides and proteins, as well as peptide and protein analogs and mimetics, can also be covalently bound to one or more of a variety of nonproteinaceous polymers, for example, polyethylene glycol, polypropylene glycol, or polyoxyalkenes, as described in U.S. Pat. Nos. 4,640,835; 4,496,689; 4,301,144; 4,670,417; 4,791,192; and 4,179,337.

Other peptide and protein analogs and mimetics within the scope of the disclosure include glycosylation variants, and covalent or aggregate conjugates with other chemical moieties. Covalent derivatives can be prepared by linkage of functionalities to groups which are found in amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues (for example, lysine or arginine). Acyl groups are selected from the group of alkyl-moieties including C3 to C18 normal alkyl, thereby forming alkanoyl aroyl species. Covalent attachment to carrier proteins, for example, immunogenic moieties, can also be employed.

In addition to these modifications, glycosylation alterations of biologically active peptides and proteins (including a γPGA conjugate, PA-based immunogen, carrier, or component of an immunogenic conjugate or composition of the disclosure) can be made, for example, by modifying the glycosylation patterns of a peptide during its synthesis and processing, or in further processing steps. In one embodiment, this is accomplished by exposing the peptide to glycosylating enzymes derived from cells that normally provide such processing, for example, mammalian glycosylation enzymes. Deglycosylation enzymes can also be successfully employed to yield useful modified peptides and proteins within the disclosure. Also embraced are versions of a native primary amino acid sequence which have other minor modifications, including phosphorylated amino acid residues, for example, phosphotyrosine, phosphoserine, or phosphothreonine, or other moieties, including ribosyl groups or cross-linking reagents.

Peptidomimetics can also have amino acid residues that have been chemically modified by phosphorylation, sulfonation, biotinylation, or the addition or removal of other moieties, particularly those that have molecular shapes similar to phosphate groups. In some embodiments, the modifications will be useful labeling reagents, or serve as purification targets (for example, affinity ligands).

C. Specific Binding Agents

The disclosure provides specific binding agents that bind a γPGA polypeptide of *B. anthracis* or another *Bacillus* species or strain, or a γPGA conjugate as disclosed herein. The binding agent can be used to purify and detect the γPGA polypeptides, as well as for detection and diagnosis of *B. anthracis*. Examples of the binding agents are a polyclonal or monoclonal antibody (including humanized monoclonal antibody), and fragments thereof, that bind to any of the γPGA polypeptides or γPGA conjugates disclosed herein.

Monoclonal or polyclonal antibodies can be raised to recognize a γPGA polypeptide and/or a γPGA conjugate as described herein, or a analog or derivative thereof. Substantially pure γPGA conjugate suitable for use as immunogen can be prepared as described above. Monoclonal or polyclonal antibodies to the γPGA conjugate can then be prepared.

Monoclonal antibodies to the polypeptides can be prepared from murine hybridomas according to the classic method of Kohler & Milstein (*Nature* 256:495-97, 1975), or a derivative method thereof. Briefly, a mouse is repetitively inoculated with a few micrograms of the selected immunogen (for example, a γPGA conjugate) over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as the enzyme-linked immunoabsorbent assay (ELISA), as originally described by Engvall (*Meth. Enzymol.*, 70:419-39, 1980), or a derivative method thereof. Selected positive clones can be expanded and their monoclonal antibody product harvested for use. Detailed procedures for monoclonal antibody production are described in Harlow and Lane, *Using Antibodies: A Laboratory Manual*, CSHL, New York, 1999. Polyclonal antiserum containing antibodies can be prepared by immunizing suitable animals with an immunogen comprising a γPGA conjugate.

Effective antibody production (whether monoclonal or polyclonal) is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.*, 33:988-91, 1971).

Booster injections can be given at regular intervals, and antiserum harvested when the antibody titer thereof, as determined semi-quantitatively, for example, by double immunodiffusion in agar against known concentrations of the antigen, begins to fall. See, for example, Ouchterlony et al., *Handbook of Experimental Immunology*, Wier, D. (ed.), Chapter 19, Blackwell, 1973. A plateau concentration of antibody is usually in the range of 0.1 to 0.2 mg/ml of serum (about 12 μM). Affinity of the antisera for the antigen is determined by preparing competitive binding curves, as described, for example, by Fisher (*Manual of Clinical Immunology*, Ch. 42, 1980).

Antibodies of the present disclosure can be contained in blood plasma, serum, hybridoma supernatants and the like. Alternatively, the antibodies can be isolated to the extent desired by well known techniques in the art, such as, ion exchange chromatography, sizing chromatography, or affinity chromatography. The antibodies can be purified so as to obtain specific classes or subclasses of antibody, such as IgM, IgG, IgA, IgG1, IgG2, IgG3, IgG4 and the like. Antibodies of the IgG class are of use for purposes of passive protection.

Antibody fragments can be used in place of whole antibodies and can be readily expressed in prokaryotic host cells. Methods of making and using immunologically effective portions of monoclonal antibodies, also referred to as "antibody fragments," are well known and include those described in Better & Horowitz, *Methods Enzymol.* 178:476-96, 1989; Glockshuber et al., *Biochemistry* 29:1362-67, 1990; and U.S. Pat. Nos. 5,648,237; 4,946,778; and 5,455,030. Conditions whereby a polypeptide/binding agent complex can form, as well as assays for the detection of the formation of a polypeptide/binding agent complex and quantitation of binding affinities of the binding agent and polypeptide, are standard in the art. Such assays can include, but are not limited to, Western blotting, immunoprecipitation, immunofluorescence, immunocytochemistry, immunohistochemistry, fluorescence activated cell sorting, fluorescence in situ hybridization, immunomagnetic assays, ELISA, ELISPOT (Coligan et al., *Current Protocols in Immunology*, Wiley, N.Y., 1995), agglutination assays, flocculation assays, cell panning, and the like, as are well known to one of skill in the art.

The antibodies or antibody fragments of the present disclosure have a number of diagnostic and therapeutic uses. For example, the antibodies or antibody fragments can be used for passive immunotherapy, such as by administering to a subject a therapeutically effective amount of the antibody or antibody fragments. In another example, the antibodies or antibody fragments can be used as in vitro diagnostic agents in various immunoassays to test for the presence of *B. anthracis* or another *Bacillus* expressing a γPGA polypeptide in biological (for example, clinical) samples, in meat and meat products, on surfaces such as food processing surfaces, or on surfaces of items subject to security testing (for example, baggage, freight, water treatment, postage handling, transportation facilities, and the like). Useful immunoassays include, but are not limited to, agglutination assays, radioimmunoassays, ELISA, fluorescence assays, Western blots and the like. In one such assay, for example, the biological sample is contacted first with an antibody of the present disclosure which binds *Bacillus* γPGA polypeptide, and then with a labeled second antibody to detect the presence of a *Bacillus*, such as *B. anthracis*, to which the first antibody has bound. Such assays can be, for example, of direct format (where a labeled first antibody is reactive with the γPGA polypeptide), an indirect format (where a labeled second antibody is reactive with the first antibody), a competitive format (such as the addition of a labeled γPGA polypeptide), or a sandwich format (where both labeled and unlabelled antibody are utilized), as well as other formats well known to one of skill in the art.

Binding agents of this disclosure can be bound to a substrate (for example, beads, tubes, slides, plates, nitrocellulose sheets, and the like) or conjugated with a detectable moiety, or both bound and conjugated. The detectable moieties contemplated for the present disclosure can include, but are not limited to, an immunofluorescent moiety (for example, fluorescein, rhodamine), a radioactive moiety (for example, $^{32}$P, $^{125}$I, $^{35}$S), an enzyme moiety (for example, horseradish peroxidase, alkaline phosphatase), a colloidal gold moiety, and a biotin moiety. Such conjugation techniques are standard in the art (for example, see Harlow and Lane, *Using Antibodies: A Laboratory Manual*, CSHL, New York 1999; Yang et al., *Nature,* 382:319-24, 1996).

D. Pharmaceutical and Immunogenic Compositions and Uses Thereof

Pharmaceutical compositions (including therapeutic and prophylactic formulations) of a γPGA conjugate and/or a PA-based immunogen are also encompassed by the present disclosure, and include a γPGA conjugate and/or other biologically active agent as described herein, typically combined together with one or more pharmaceutically acceptable vehicles and, optionally, other therapeutic ingredients (for example, antibiotics, or anti-inflammatories).

Within the pharmaceutical compositions and methods of the disclosure, the γPGA conjugate and/or other biologically active agent can be administered to subjects by a variety of mucosal administration modes, including by oral, rectal, intranasal, intrapulmonary, or transdermal delivery, or by topical delivery to other surfaces. Optionally, the γPGA conjugate and/or other active agent can be administered by non-mucosal routes, including by intramuscular, subcutaneous, intravenous, intra-atrial, intra-articular, intraperitoneal, or parenteral routes. In other alternative embodiments, the γPGA conjugate and/or other active agent can be administered ex vivo by direct exposure to cells, tissues or organs originating from a subject.

To formulate pharmaceutical compositions of the present disclosure, the γPGA conjugate and/or other biologically active agent can be combined with various pharmaceutically acceptable additives, as well as a base or vehicle for dispersion of the γPGA conjugate and/or other biologically active agent Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton Ind.) and IL-12 (Genetics Institute, Cambridge Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The γPGA conjugate and/or other biologically active agent can be dispersed in a base or vehicle, which can include a hydrophilic compound having a capacity to disperse the γPGA conjugate and/or other biologically active agent, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including, fluid or viscous solutions, gels, pastes, powders, microspheres and films for direct application to a mucosal surface.

The γPGA conjugate and/or other biologically active agent can be combined with the base or vehicle according to a variety of methods, and release of the γPGA conjugate and/or other biologically active agent can be by diffusion, disintegration of the vehicle, or associated formation of water channels. In some circumstances, the γPGA conjugate and/or other biologically active agent is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the γPGA conjugate and/or other biologically active agent can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the γPGA conjugate and/or other biologically active agent can be brought about by including in the composition an agent which delays absorption, for example, monostearate salts and gelatin.

In certain embodiments, the γPGA conjugate and/or other biologically active agent can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the γPGA conjugate and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DLlactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly (epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the γPGA conjugate and/or other biologically active agent in the required amount in an appropriate solvent with one or a combination of ingredients enumerated herein, as required, followed by filtered sterilization. Generally, dispersions are prepared by incorporating the γPGA conjugate and/or other biologically active agent into a sterile vehicle that contains a basic dispersion medium and the required other ingredients from those enumerated herein. In the case of sterile powders, methods of preparation include vacuum drying and freeze-drying which yields a powder of the γPGA conjugate and/or other biologically active agent plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the γPGA conjugate and/or other biologically active agent can be delivered to a subject in a manner consistent with conventional methodologies associated with management of the disorder for which treatment or prevention is sought. In accordance with the disclosure herein, a prophylactically or therapeutically effective amount of the γPGA conjugate and/or other biologically active agent is administered to a subject in need of such treatment for a time and under conditions sufficient to prevent, inhibit, and/or ameliorate a selected disease (for example, anthrax) or condition or one or more symptom(s) thereof.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, anthrax) as discussed herein, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure. In accordance with these methods and principles, a γPGA conjugate and/or other biologically active agent can be administered according to the teachings herein as an independent prophylaxis or treatment program, or as a follow-up, adjunct or coordinate treatment regimen to other treatments, including surgery, vaccination, immunotherapy, hormone treatment, cell, tissue, or organ transplants, and the like.

The γPGA conjugates can be used in coordinate vaccination protocols or combinatorial formulations with PA-based immunogens to enhance an immune response elicited by a PA-based immunogen alone. In exemplary embodiments, γPGA-rPA induces both anti-PA and anti-γPGA immune responses. In other embodiments, novel combinatorial immunogenic compositions and coordinate immunization protocols employ separate immunogens or formulations, each directed toward eliciting an anti-PA or an anti-γPGA immune response. Separate immunogens that elicit the anti-PA or anti-γPGA immune response can be combined in a polyvalent immunogenic composition administered to a subject in a single immunization step, or they can be administered separately (in monovalent immunogenic compositions) in a coordinate immunization protocol. Typically, when the anti-PA and anti-γPGA immunogens are administered separately, they are administered coordinately, in close temporal sequence (for example, the anti-PA immunogen will be administered hours, one or two days, or within a week or two, prior to administration of the anti-γPGA immunogen, or vice versa).

The administration of the γPGA conjugate and/or other biologically active agent of the disclosure can be for either prophylactic or therapeutic purpose. When provided prophylactically, the γPGA conjugate and/or other biologically active agent is provided in advance of any symptom. The prophylactic administration of the γPGA conjugate and/or other biologically active agent serves to prevent or ameliorate any subsequent infection. When provided therapeutically, the γPGA conjugate and/or other biologically active agent is provided at (or shortly after) the onset of a symptom of disease or infection. The γPGA conjugate and/or other biologically active agent of the disclosure can thus be provided prior to the anticipated exposure to *B. anthracis* or another *Bacillus*, so as to attenuate the anticipated severity, duration or extent of an infection and/or associated disease symptoms, after exposure or suspected exposure to the bacteria, or after the actual initiation of an infection.

For prophylactic and therapeutic purposes, the γPGA conjugate and/or other biologically active agent disclosed herein can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the γPGA conjugate and/or other biologically active agent can be provided as repeated doses within a prolonged prophylaxis or treatment regimen, that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using ice vitro models (for example, immunologic and histopathologic assays). Using such models, only ordinary calculations and adjustments are required to determine an appropriate concentration and dose to administer a therapeutically effective amount of the γPGA conjugate and/or other biologically active agent (for example, amounts that are effective to elicit a desired immune response or alleviate one or more symptoms of a targeted disease). In alternative embodiments, an effective amount or effective dose of the γPGA conjugate and/or biologically active agent may simply inhibit or enhance one or more selected biological activities correlated with a disease or condition, as set forth herein, for either therapeutic or diagnostic purposes.

The actual dosage of the γPGA conjugate and/or other biologically active agent will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the γPGA conjugate and/or other biologically active agent for eliciting the desired activity or biological response in the subject. Dosage regimens can be adjusted to provide an optimum prophylactic or therapeutic response. A therapeutically effective amount is also one in which any toxic or detrimental side effects of the γPGA conjugate and/or other biologically active agent is outweighed in clinical terms by therapeutically beneficial effects. A non-limiting range for a therapeutically effective amount of a γPGA conjugate and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight. The antibodies of the present disclosure will typically be administered in a dosage ranging from about 1 mg/kg body weight to about 10 mg/kg body weight of the subject, although a lower or higher dose can be administered.

Upon administration of a γPGA conjugate (for example, γPGA-PA) or related immunogenic composition of the disclosure (for example, via injection, aerosol, oral, topical or other route), the immune system of the subject typically responds to the immunogenic composition by producing antibodies specific for γPGA and/or PA. Such a response signifies that an immunologically effective dose of the γPGA conjugate or related immunogenic composition was delivered. An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the γPGA conjugate and/or other biologically active agent. In some embodiments, the antibody response of a subject administered the compositions of the disclosure will be determined in the context of evaluating effective dosages/immunization protocols. In most instances it will be sufficient to assess the antibody titer in serum or plasma obtained from the subject. Decisions as to whether to administer booster inoculations and/or to change the amount of the composition administered to the individual can be at least partially based on the antibody titer level. The antibody titer level can be based on, for example, an immunobinding assay which measures the concentration of antibodies in the serum which bind to a specific antigen, for example, γPGA and/or PA. The ability to neutralize in vitro and in vivo biological effects of the B. anthracis can also be assessed to determine the effectiveness of the treatment.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

The methods of using γPGA conjugates, and the related compositions and methods of the disclosure, are useful in increasing resistance to, preventing, ameliorating, and/or treating infection and disease caused by bacilli in animal hosts, and other, in vitro applications. In exemplary embodiments, the methods and compositions are useful in increasing resistance to, preventing, ameliorating, and/or treating infection and disease caused by B. anthracis infection in animals and humans. These immunogenic compositions can be used for active immunization for prevention of B. anthracis infection, and for preparation of immune antibodies. In one embodiment, the immunogenic compositions and methods are designed to confer specific immunity against infection with B. anthracis, and to induce antibodies specific to B. anthracis γPGA. The immunogenic compositions are composed of non-toxic components, suitable for infants, children of all ages, and adults.

The methods of the disclosure are broadly effective for treatment and prevention of bacterial disease and associated inflammatory, autoimmune, toxic (including shock), and chronic and/or lethal sequelae associated with bacterial infection. In selected embodiments, one or more symptoms or associated effects of exposure to and/or infection with anthrax is/are prevented or treated by administration to a mammalian subject at risk of acquiring anthrax, or presenting with one or more anthrax symptom(s), of an effective amount of a γPGA conjugate of the disclosure. Therapeutic compositions and methods of the disclosure for prevention or treatment of toxic or lethal effects of bacterial infection are applicable to a wide spectrum of infectious agents. Non-lethal toxicities that will be ameliorated by these methods and compositions can include fatigue syndromes, inflammatory/autoimmune syndromes, hypoadrenal syndromes, weakness, cognitive symptoms and memory loss, mood symptoms, neurological and pain syndromes and endocrine symptoms. Any significant reduction or preventive effect of the γPGA conjugate with respect to the foregoing disease condition(s) or symptom(s) administered constitutes a desirable, effective property of the subject composition/method of the disclosure.

The compositions and methods of the disclosure are particularly useful for treatment and prevention of infection and toxic/morbidity effects of exposure to anthrax and/or other disease- or illness-causing bacilli. Additional embodiments of the disclosure are directed to diagnostic compositions and methods to identify individuals at risk for exposure, infection, toxic effects, or long term deleterious effects of exposure to pathogenic bacteria, for example B. anthracis. In additional aspects of the disclosure, the methods and compositions disclosed herein are useful for identification of environmental agents, including *B. anthracis* and other bacilli expressing a γPGA, including food-borne pathogenic bacilli. Certain individuals exposed to small amounts of bacterial products, such as those derived from *B. anthracis*, presenting certain genetic or physiological backgrounds, are predisposed to development of chronic syndromes, including fatigue syndromes, inflammatory/autoimmune syndromes, hypoadrenal syndromes, weakness, cognitive symptoms and memory loss, mood symptoms, neurological and pain syndromes and endocrine symptoms. In this context, the methods and compositions of the disclosure are employed to detect, and alternatively to treat and/or ameliorate, such ubiquitous environmental exposures and associated symptoms. For example, antibodies of the disclosure provide for screening for γPGA in mammalian subjects or food products at risk of contact/infection with a *Bacillus* that expresses a γPGA.

In related embodiments, the disclosure provides compositions, including but not limited to, mammalian serum, plasma, and immunoglobulin fractions, which contain antibodies that are immunoreactive with a γPGA of *B. anthracis* or another *Bacillus* species or strain. These antibodies and antibody compositions can be useful to prevent, treat, and/or ameliorate infection and disease caused by the microorganism. The disclosure also provides such antibodies in isolated form. In exemplary embodiments, high titer anti-γPGA sera, antibodies isolated therefrom, or monoclonal antibodies, can be used for therapeutic treatment for patients with infection by *B. anthracis* or another *Bacillus* species or strain. Antibodies elicited by the agents of this disclosure can be used for the treatment of established *B. anthracis* or other *Bacillus* infections, and can also be useful in providing passive protection to an individual exposed to *B. anthracis* or another *Bacillus*.

The instant disclosure also includes kits, packages and multi-container units containing the herein described pharmaceutical compositions, active ingredients, and/or means for administering the same for use in the prevention and treatment of anthrax and other bacterial diseases and other conditions in mammalian subjects. Kits for diagnostic use are also provided. In one embodiment, these kits include a container or formulation that contains one or more of the γPGA conjugates and/or other active agent described herein. In one example, this component is formulated in a pharmaceutical preparation for delivery to a subject. The γPGA conjugate and/or other biologically active agent is/are optionally contained in a bulk dispensing container or unit or multi-unit dosage form. Optional dispensing means can be provided, for example a pulmonary or intranasal spray applicator. Packaging materials optionally include a label or instruction indicating for what treatment purposes (for example, anthrax) and/or in what manner the pharmaceutical agent packaged therewith can be used.

The subject matter of the present disclosure is further illustrated by the following non-limiting Examples.

EXAMPLES

Example 1

Materials and Methods

Bacterial Strains

*B. pumilus*, strain Sh18 (Goodman et al., *Biochem.* 7:706-10, 1968), and *B. anthracis* strain A34, a pX01⁻, pX02⁺ variant derived from the Ames strain by repeated passage at 43° C., are described by Klein et al. (*Science* 138:1331-33, 1962).

Poly-γ-Glutamic Acid

γPGA was extracted from culture supernatants of *B. anthracis* or *B. pumilus* by acidification to pH 1.5, precipitation with ethanol, and passage through a 2×100 cm Sepharose CL-4B column in 0.2 M NaCl (Myerowitz et al., *Infect. Immun.* 8:896-900, 1973). The composition of each γPGA was confirmed by $^1$H-NMR and $^{13}$C-NMR and their enantiomeric compositions were determined by GLC-MS spectroscopy.

Analyses

Amino acid analyses were conducted by GLC-MS after hydrolysis with 6 N HCl, 150° C., 1 hour, derivatization to heptafluorobutyryl R-(−)isobutyl esters and assayed with a Hewlett-Packard apparatus (Model HP 6890) with a HP-5 0.32×30 mm glass capillary column, temperature programming at 8° C./min, from 125° C. to 250° C. in the electron ionization (106 eV) mode (MacKenzie, *J. Assoc. Off. Anal. Chem.* 70:151-60, 1987). Under these conditions, D-glutamic acid is separated from the L-enantiomer so that the ratio of each can be calculated based on the ratio of D-glutamic acid relative to L-glutamic acid residues in the protein (FIG. 1). The number of peptide chains in L-peptide conjugates was calculated by the relative increase of total L-glutamic acid relative to aspartic acid. Protein concentration was measured by the method of Lowry et al. (*J. Biol. Chem.* 193:266-73, 1951), free ε amino groups by Fields' assay (*Biochem. J.* 124:581-90, 1971), thiolation by release of 2-pyridylthio groups ($A_{343}$) (Carlsson et al, *Biochem. J.* 173:723-37, 1978), and hydrazide as reported by Schneerson et al. (*J. Exp. Med.* 152:361-76, 1980). SDS-PAGE employed 14% gels according to the manufacturer's instructions. Double immunodiffusion was performed in 1.0% agarose gel in PBS.

MALDI-TOF

Mass spectra were obtained with a PerSeptive BioSystems Voyager Elite DE-STR MALDI-TOF instrument (PE Biosystems, Framingham, Mass.) operated in the linear mode, 25 kV accelerating voltage and a 300 nanosecond ion extraction delay time. Samples for analysis were prepared by a "sandwich" of matrix and analyte. First, 1 μl matrix (saturated solution of sinnapinic acid made in 1:1 $CH_3CN$ and 0.1% trifluroacetic acid) was dried on the sample stage. Second, 1 μl of sample and an additional 1 μl of matrix was applied. After the "sandwich" was dried, the sample was placed in the mass spectrometer.

Antigens

BSA (Sigma Chemical Co., St. Louis, Mo.) was dialyzed against pyrogen-free water, sterile-filtered, and freeze-dried. Recombinant Protective Antigen from *B. anthracis* and recombinant exotoxin A from *P. aeruginosa* were prepared and characterized as described by Ramirez et al. (*J. Ind. Microbiol. Biotechnol.* 28:232-38, 2002) and Johansson et al. (*J. Biotechnol.* 48:9-14, 1996). Exemplary synthetic polypeptides of γPGA (AnaSpec, San Jose, Calif.) were synthesized by the method of Merrifield, with lengths of 5, 10, 15, or 20 residues. Their purity and authenticity were verified by GLC-MS, LC-MS and MALDI-TOF. γPGA polypeptides were bound to carrier proteins at either the C- or the N-termini (—C indicates that the C-terminus is free; N— indicates that the amino-terminus is free). All reactions were conducted in a pH stat under argon.

| Type I: | NBrAc-Gly₃-γDPGA$_n$-COOH(Br-Gly₃-γDPGA$_n$-C) |
|---|---|
| | NBrAc-Gly₃-γLPGA$_n$-COOH(Br-Gly₃-γLPGA$_n$-C) |

-continued

| Type II: | NAc-L-Cys-Gly$_3$-γDPGA$_n$-COOH(Cys-Gly$_3$-γDPGA$_n$-C) |
| | NAc-L-Cys-Gly$_3$-γLPGA$_n$-COOH(Cys-Gly$_3$-γLPGA$_n$-C) |
| Type III: | NAc-γDPGA$_n$-Gly$_3$-L-Cys-CONH$_2$(N-γDPGA$_n$-Gly$_3$-Cys) |
| | NAc-γLPGA$_n$-Gly$_3$-L-Cys-CONH$_2$(N-γLPGA$_n$-Gly$_3$-Cys) |
| Type IV: | CHO-Gly$_3$-γDPGA$_n$-COOH |
| Type V: | NAc-γDPGA$_n$-Gly$_3$-CO-AH |
| | NAc-γDPGA$_n$-CO-AH |
| Type VI: | NAc-γDPGA$_n$-Cys-CONH$_2$ |

Conjugation of BSA, rEPA and rPA with *B. anthracis* γDPGA and *B. pumilus* γDLPGA BSA, rEPA and rPA were derivatized with adipic acid dihydrazide with modifications (Schneerson et al., *J. Exp. Med.* 152:361-76, 1980). The pH was maintained at 7.0 and 0.1 M EDAC used. The products, BSA-AH, rEPA-AH and rPA-AH, contained 2.0-4.8% hydrazide.

γPGA was bound to rPA-AH or rEPA-AH with 0.01 M EDAC, the reaction mixture passed through a 1×90 cm Sephacryl S-1000 column in 0.2 M NaCl, and fractions reacting with anti-PA and anti-γDPGA by an identity line were pooled.

Conjugation of Type I Peptide with rPA via Thioether Bond

Step 1: Derivatization of BSA, rEPA and rPA with SPDP

To rPA (30 mg) in 1.5 ml of Buffer A' (PBS, 3% glycerol, 0.005 M EDTA, pH 7.6), SPDP (10 mg) in 50 µl dimethyl sulfoxide (DMSO) was added in 10 µl aliquots and reacted for 1 hour at pH 7.6. The product, 2-pyridyldithio-propionyl-rPA (PDP-rPA) was passed through a 1×48 cm Sephadex G-50 column in Buffer A (PBS, 0.05% glycerol 0.005 M EDTA, pH 7.6), and protein-containing fractions were pooled and assayed for thiolation, antigenicity, and molecular mass (Carlsson et al, *Biochem. J.* 173:723-37, 1978).

Step 2: Conjugation of PDP-Protein with Type I Peptide

PDP-protein (24 mg) in 2 ml Buffer A was treated with 50 mM dithiothreitol for 30 minutes at room temperature and passed through a 1×48 cm Sephadex G-50 column in Buffer A. Fractions containing the 3-thiopropionyl-ε-Lys-NH$_2$-rPA (rPA-SH) were collected, concentrated to 1.5 ml and glycerol added to a final concentration of 3%. Br-Gly$_3$-γ-DPGA$_n$-C, 10 mg in 1 ml of Buffer A, was adjusted to pH 7.6 and rPA-SH added, incubated for 1 hour at room temperature (Inman et al., *Bioconj. Chem.* 2:458-63, 1991), transferred to a vial, capped and tumbled overnight at room temperature. Bromoacetamide, 0.5 mg in 50 µl Buffer A, was added to block unreacted thiols. After 30 minutes, the reaction mixture was passed through a 1×90 cm Sephacryl S-200 column in Buffer B (0.01 M phosphate, 0.2 M NaCl, 0.05% glycerol, pH 7.2). Fractions containing protein-γPGA were pooled and assayed for peptide and protein concentration, antigenicity, and molecular mass.

Products:

BSA contained 60, rPA contained 58 and rEPA contained 15 moles Lys per mole of protein, respectively. Under these conditions, 28 of 60 ε-Lys-NH$_2$ of BSA, 50-55 of 58 of rPA and 15 of 15 of rEPA were derivatized with SPDP with retention of their antigenicity. Conjugation of BSA-SH, rPA-SH and rEPA-SH with Type I peptides yielded:

BSA-SH/Gly$_3$-γDPGA$_n$-C
BSA-SH/Gly$_3$-γLPGA$_n$-C
rEPA-SH/Gly$_3$-γDPGA$_n$-C
rPA-SH/Gly$_3$-γDPGA$_n$-C

Conjugation with Type II, III and VI Peptides

Step 1: Derivatization of Protein with SBAP rPA or rEPA (30 mg) in 1.5 ml of Buffer A' was adjusted to pH 7.2. SBAP (11 mg) in 50 µl DMSO was added in 10 µl aliquots (Inman et al., *Bioconj. Chem.* 2:458-63, 1991). After 60 minutes, the reaction mixture was passed through a 1×90 cm Sepharose CL-6B column in Buffer B. Fractions containing bromoacetamidopropionyl-ε-Lys-NH-rPA (Br-rPA) were collected and assayed for protein, free —NH$_2$, antigenicity, and molecular mass.

Step 2: Conjugation of Br-Protein with Type II, III and VI Peptides

Type II, III or VI peptides, 5 to 15 mg in Buffer A, were adjusted to pH 7.6 with 1 N NaOH. Br-protein (25 mg) in 1.5 ml Buffer A' was added. After 1 hour, the reaction mixture was transferred to a vial, capped, and tumbled overnight at room temperature. γ-mercaptoethanol (1 µl) was added to quench the remaining bromoacetyl groups in Br-protein. After 30 minutes, the reaction mixture was passed through 1×90 cm Sepharose CL-6B column in Buffer B. Fractions containing protein-γPGA were pooled and assayed for peptide and protein concentration, antigenicity, and molecular mass.

Products:

Under these conditions, 50-55 of 58 and 15 of 15 residues of ε-Lys-NH$_2$ of rPA and rEPA, respectively, were modified with SBAP. rPA$_{form}$ had 30 out of 58 ε-Lys-NH$_2$ free, and derivatization with SBAP converted essentially all 30 γ-Lys-NH$_2$ into the bromoacylated derivative, Br-rPA$_{form}$.

Conjugation of Br-rPA and Br-rEPA with Type II peptides yielded 4 conjugates:

rPA/S-Cys-Gly$_3$-γDPGA$_n$-C
rPA/S-Cys-Gly$_3$-γLPGA$_n$-C
rEPA/S-Cys-Gly$_3$-γDPGA$_n$-C
rEPA/S-Cys-Gly$_3$-γLPGA$_n$-C

Conjugation of Br-rPA and Br-rEPA with Type III peptides yielded 4 conjugates:

N-γDPGA$_n$-Gly$_3$-Cys-S/rPA
N-γLPGA$_n$-Gly$_3$-Cys-S/rPA
N-γDPGA$_n$-Gly$_3$-Cys-S/rEPA
N-γLPGA$_n$-Gly$_3$-Cys-S/rEPA

All eight conjugates precipitated with an identity reaction with their protein and γPGA, antisera by immunodiffusion. Representative analysis by MALDI-TOF is shown in FIG. 2.

Conjugation of Br-rEPA with Type VI peptide yielded:

rEPA/Cys-γDPGA$_n$-N

Conjugation of Br-rPA$_{form}$ with the N-γDPGA$_n$-Gly$_3$-Cys Type III peptide yielded:

rPA$_{form}$/Cys-Gly$_3$-γDPGA$_n$-N

Conjugation of Type IV Peptide with BSA, rEPA and rPA via Hydrazone Linkage 4-formylbenzoyl-γDPGA (CHO-γDPGA) was bound to BSA-AH, rEPA-AH or rPA-AH in phosphate buffer, pH 7.0, at a molar ratio of CHO-γDPGA to carrier protein-AH of 2:1 for 24-48 hours at room temperature. The reaction mixture was passed through a 1×90 cm Sepharose CL-6B column in 0.2 M phosphate buffer, pH 7.0, and fractions reacting with anti-carrier protein and anti-γDPGA antibodies were pooled.

Conjugation of BSA-AH, rEPA-AH or rPA-AH with Type IV peptides yielded:

BSA-AH/CHO-Gly$_3$-γDPGA$_n$-C
rEPA-AH/CHO-Gly$_3$-γDPGA$_n$-C
rPA-AH/CHO-Gly$_3$-γDPGA$_n$-C

Conjugation of Type V Peptide with BSA, rEPA, rPA, rPA$_{form}$ via Hydrazone Linkage Step 1: Derivatization of BSA, rEPA, rPA, or rPA$_{form}$ with SFB To BSA (30 mg) in 1.2 ml of Buffer A containing 1% glycerol, SFB (7.5 mg) in 100 µl DMSO was added and reacted for 1 hour at pH 7.6. The product, 4-formylbenzoyl-BSA (CHO-BSA), was passed through a 1×48 cm Sephadex G-50 column in Buffer A. Protein containing fractions were pooled and assayed for the presence of benzoylaldehyde, antigenicity and protein concentration. For rPA, rEPA and rPA$_{form}$, derivatization with SFB was performed using 4 mg/ml rPA, rEPA and rPA$_{form}$, respectively.

Step 2: Conjugation of CHO-BSA, CHO-rEPA, CHO-rPA or CHO-rPA$_{form}$ with Type V Peptides To CHO-BSA, CHO-rEPA, CHO-rPA or CHO-rPA$_{form}$ (20 mg) in 1.25 ml of Buffer A, 20 mg of Type V peptides dissolved in 400 µl of 1M phosphate buffer, pH 7.4, was added. The pH of the reaction mixture was adjusted to 7.0 and incubated for 48-72 hours at room temperature. The mixture was passed through a 1×90 cm Sepharose CL-6B column in Buffer A, and fractions reacting with anti-carrier protein and anti-γDPGA antibodies were pooled.

Products:

rPA$_{form}$ had 30 out of 58 ε-Lys-NH$_2$ free (28 Lys were modified by the formaldehyde treatment), and the derivatization with SFB converted essentially all 30 ε-Lys-NH$_2$ into 4-formylbenzoyl-rPA$_{form}$ (CHO-rPA$_{form}$). Conjugation of CHO-BSA, CHO-rEPA, CHO-rPA or CHO-rPA$_{form}$ with Type V peptides yielded:

BSA-CHO/AH-Gly$_3$-γDPGA$_n$-N
rEPA-CHO/AH-γDPGA$_n$-N
rPA-CHO/AH-γDPGA$_n$-N
rPA$_{form}$-CHO/AH-Gly$_3$-γDPGA$_n$-N Conjugation of BSA-CHO/AH with Type IV Peptide via Hydrazone Linkage Step 1: Derivatization of BSA with SLV To BSA (56 mg) in 2.0 ml of Buffer A was added SLV (20 mg) in 200 µl DMSO at pH 7.6 and reacted for 1 hour at room temperature. The product, BSA-LV-CHO, was passed through a 1×48 cm Sephadex G-50 column in Buffer A. Protein containing fractions were pooled and assayed for protein concentration.

Step 2: Derivatization of BSA-LV-CHO with ADH

BSA-LV-CHO (35 mg) in 1.5 ml of 0.2 M phosphate buffer, pH 6.0, was reacted with adipic acid dihydrazide (250 mg) at pH 6.0 in the presence of 100 µl of borane-hydride-pyridine complex (800 µmoles) for 48 hours. The product, BSA-LV-CHO/AH, was passed through a 1×48 cm Sephadex G-50 column in Buffer A. BSA containing fractions were collected, analyzed for protein concentration, and the degree of -AH derivatization.

Step 3: Conjugation of BSA-LV-CHO/AH with Type IV Peptide

BSA-LV-CHO/AH (20 mg) in 1.5 ml of 0.2 M phosphate buffer, pH 6.0, was mixed with 10 mg Type IV peptide, pH 6.0. After 60 minutes, 100 µl of borane-hydride-pyridine complex (800 µmoles) was added, and after 48 hours the product was passed through a 1×48 cm Sephadex G-50 column in Buffer A. Fractions reacting with anti-BSA and anti-γDPGA antibodies were pooled.

Conjugation of BSA-LV-CHO/AH with Type IV peptide yielded:

BSA-SL-AH/CHO-Gly$_3$-γDPGA$_n$-C

Immunization

Five- to six-week old female NIH GP mice were immunized s.c. 3 times at 2-week intervals with 2.5 µg γPGA as a conjugate in 0.1 ml of PBS, and groups of 10 mice were exsanguinated 7 days after the second or third injections (Schneerson et al, *J. Exp. Med.* 152:361-76, 1980). Controls received PBS.

Antibodies

Serum IgG antibodies were measured by ELISA (Taylor et al, *Infect. Immun.* 61:3678-87, 1993). Nunc Maxisorb plates were coated with γDPGA, 20 µg/ml PBS or 4 µg rPA/ml PBS. Plates were blocked with 0.5% BSA (or with 0.5% HSA for assay of BSA conjugates) in PBS for 2 hours at room temperature. A MRX Dynatech reader was used. Antibody levels were calculated relative to standard sera: for γDPGA, a hyper-immune murine serum, prepared by multiple i.p. injections of formalin-treated *B. anthracis* strain A34 and assigned a value of 100 ELISA units (EU), for PA a mAb containing 4.7 mg Ab/ml (Little et al., *Infect. Immun.* 56:1807-13, 1988). Results were computed with an ELISA data processing program provided by the Biostatistics and Information Management Branch, CDC (Plikaytis et al., *User's Manual* 12 *CDC*, Version 1.00, 1996). IgG levels are expressed as geometric mean (GM).

Opsonophagocytosis

Spores of *B. anthracis*, strain A34, were maintained at $5 \times 10^8$ spores per ml in 1% phenol. The human cell line, HL-60 (CCL240, ATCC, Rockville, Md.) was expanded and differentiated by dimethyl formamide into 44% myelocytes and metamyelocytes, and 53% band and polymorphonuclear leukocytes (PMLs). PMLs were at an effector/target cell ratio of 400:1. PMLs were centrifuged and resuspended in opsonophagocytosis buffer (Hanks' buffer with $Ca^{2+}$, $Mg^{2+}$ and 0.1% gelatin (Life Technologies, Grand Island, N.Y.)) at $2 \times 10^7$ cells per ml. Spores were cultured at $5 \times 10^7$ spores per ml for 3 hours in 20% $CO_2$, and diluted to $5 \times 10^4$ spores per ml. Sera were diluted 2-fold with 0.05 ml of opsonophagocytosis buffer, and 0.02 ml (containing approximately $10^3$ bacteria) were added to each well of a 24-well tissue culture plate (Falcon, Franklin Lakes, N.J.). The plates were incubated at 37° C. in 5% $CO_2$ for 15 min. A 0.01 ml of aliquot of colostrum-deprived baby calf serum (complement) and 0.02 ml of HL-60 suspension containing $4 \times 10^5$ cells was added to each well, and incubated at 37° C. in 5% $CO_2$ with mixing at 220 rpm for 45 minutes. A 0.01 ml aliquot from each well was added to tryptic soy agar at 50° C., and CFU determined the next morning.

Opsonophagocytosis was defined by ≧50% killing compared with the growth in control wells (Romero-Steiner et al., *Clin. Diagn. Lab. Immunol.* 4:415-33, 1997).

Statistics

ELISA values are expressed as the GM. An unpaired t test was used to compare GMs in different groups of mice.

Example 2

Serum IgG Anti-γDPGA Antibodies

This example demonstrates that conjugates of *B. anthracis* γDPGA and of *B. pumilus* γD/LPGA elicited IgG anti-γD-PGA antibodies.

Native γDPGA from the capsule of *B. anthracis* elicited trace levels of antibodies after the third injection (Table 1). All the conjugates, in contrast, elicited IgG anti-γDPGA antibodies after two injections (Table 1). Conjugates of *B. anthracis* γDPGA and of *B. pumilus* γD(60%)/L(40%)PGA elicited IgG anti-γDPGA antibodies of intermediate levels after two injections with a booster after the third (Table 1). However, precipitates were formed during the synthesis of both conjugates, resulting in low yields. This problem was not encountered when preparing the synthetic γPGA conjugates.

The highest levels of anti-γDPGA antibodies were achieved with peptide decamers at a density (peptide chains to carrier molecule) of 16:1 for rPA/Cys-Gly$_3$-γDPGA$_{10}$-C, and of 11:1 and 14:1 for rPA-SH/Gly$_3$-γDPGA$_{10}$-C (Table 1). rPA was a more effective carrier than rEPA or BSA (Table 1). With the exception of rPA-SH/Gly$_3$-γDPGA$_{10}$-C, with 11 chains per carrier protein, all conjugates elicited a rise in anti-γDPGA antibodies after the third injection (Table 1). Conjugates prepared with L peptides bound at either the C- or N-terminus induced low levels of IgG anti-γDPGA antibodies (Table 1).

A dose response of two γDPGA conjugates with rPA and rEPA as the carrier showed that rPA was a more effective carrier than rEPA (Table 2). Both peptides had 20 glutamic acid residues, and similar number of chains per carrier protein. The lowest dose (2.5 µg) of rPA-SH/Gly$_3$-γDPGA-C elicited the highest level of IgG anti-γDPGA antibodies (9, 133 EU, Table 2). The levels declined about half that at the 20 µg dose (Table 2). rEPA-SH/Gly$_3$-γDPGA-C, in contrast, elicited similar levels at all dosages (Table 2).

TABLE 2

Dose/immunogenicity relation of conjugates prepared with 20-mers of γDPGA bound to rPA or rEPA.

| Conjugate | Mol γDPGA/ mol protein | Protein/ γDPGA (wt/wt) | Dose/ mice (µg γDPGA) | Anti- γDPGA 3$^{rd}$ injection |
|---|---|---|---|---|
| rPA-SH/Gly$_3$-γDPGA$_{20}$-C | 8 | 1:0.25 | 2.5 | 9152 |
|  |  |  | 5 | 7070 |
|  |  |  | 10 | 3487 |
|  |  |  | 20 | 4901 |

TABLE 1

Composition and serum geometric mean IgG anti-γDPGA and anti-carrier protein antibodies elicited in mice by conjugates of γPGA with BSA, rEPA and rPA.

| Conjugate | Mol γDPGA per mol protein | Protein per γDPGA (wt/wt) | Anti-γDPGA* Second injection | Anti-γDPGA* Third injection | Anti-protein† Second injection | Anti-protein† Third injection |
|---|---|---|---|---|---|---|
| γDPGA-*B. anthracis* | NA‡ | NA | 0.3 | 4.4 | NA | NA |
| rEPA-AH/γDPGA-*B. anthracis* | NA | 1:0.29 | 695 | 2312 | ND§ | ND |
| rPA-AH γDPGA-*B. anthracis* | NA | 1:4.42 | 1325 | 3108 | ND | ND |
| BSA-SH/Gly$_3$-γDPGA$_{10}$-C¶ | 7 | 1:0.14 | 134 | 1984 | ND | ND |
| BSA-SH/Gly$_3$-γDPGA$_{10}$-C | 18 | 1:0.35 | 1882 | 1821 | ND | ND |
| BSA-SH/Gly$_3$-γDPGA$_{10}$-C | 25 | 1:0.49 | 2063 | 2780 | ND | ND |
| BSA-SH/Gly$_3$-γLPGA$_{10}$-C | 7 | 1:0.14 | 261 | 618 | ND | ND |
| rEPA/Cys-Gly$_3$-γDPGA$_{10}$-C | 7 | 1:0.14 | 479 | 4470 | ND | ND |
| rEPA-SH/Gly$_3$-γDPGA$_5$-C | 17 | 1:0.17 | 502 | 1168 | ND | ND |
| rEPA-SH/Gly3-γDPGA$_{10}$-C | 9 | 1:0.18 | 931 | 3193 | ND | ND |
| rEPA-SH/Gly3-γDPGA$_{20}$-C | 5 | 1:0.19 | 749 | 2710 | ND | ND |
| rPA/Cys-Gly$_3$-γDPGA$_5$-C | 32 | 1:0.26 | 2454 | 4560 | 0.06 | 8.5 |
| rPA/Cys-Gly$_3$-γDPGA$_{10}$-C | 16 | 1:0.26 | 9091 | 11268 | 1.30 | 59.3 |
| rPA/Cys-Gly$_3$-γDPGA$_{20}$-C | 14 | 1:0.44 | 742 | 3142 | 0.01 | 4.5 |
| rPA/Cys-Gly$_3$-γDPGA$_5$-N | 22 | 1:0.18 | 3149 | 3460 | 3.70 | 95.0 |
| rPA/Cys-Gly$_3$-γDPGA$_{10}$-N | 21 | 1:0.33 | 5489 | 7516 | 0.10 | 2.2 |
| rPA/Cys-Gly$_3$-γDPGA$_{20}$-N | 8 | 1:0.25 | 2630 | 5461 | 0.05 | 4.9 |
| rPA-SH/Gly$_3$-γDPGA$_5$-C | 15 | 1:0.12 | 1813 | 3607 | 0.27 | 19.7 |
| rPA-SH/Gly$_3$-γDPGA$_{10}$-C | 11 | 1:0.18 | 10460 | 9907 | 0.50 | 102.0 |
| rPA-SH/Gly$_3$-γDPGA$_{10}$-C | 14 | 1:0.22 | 4378 | 7206 | 0.34 | 66.3 |
| rPA-SH/Gly$_3$-γDPGA$_{20}$-C | 4 | 1:0.13 | 2655 | 4069 | 0.90 | 32.2 |
| rPA-SH/Gly$_3$-γDPGA$_{20}$-C | 8 | 1:0.25 | 9672 | 7320 | 0.22 | 189.0 |
| rPA/Cys-Gly$_3$-γLPGA$_{20}$-N | 22 | 1:0.70 | 24 | 79 | 0.14 | 3.0 |
| rPA/Cys-Gly$_3$-γLPGA$_{20}$-C | 24 | 1:0.76 | 155 | 437 | 0.31 | 7.8 |
| BSA-AH/CHO-Gly$_3$-γDPGA$_{10}$-C | 12 | 1:0.23 | 1476 | 3354 | ND | ND |
| rEPA-AH/CHO-Gly$_3$-γDPGA$_{10}$-C | 8 | 1:0.15 | 807 | 2099 | 1 | 14 |
| rPA-AH/CHO-Gly$_3$-γDPGA$_{10}$-C | 22 | 1:0.34 | ND | ND | ND | ND |
| BSA-CHO/AH-Gly$_3$-γDPGA$_{10}$-N | 8 | 1:0.17 | 185 | 1139 | ND | ND |
| rEPA-CHO/AH-γDPGA$_{15}$-N | 6 | 1:0.18 | ND | ND | ND | ND |
| rPA-CHO/AH-γDPGA$_{15}$-N | 5 | 1:0.12 | ND | ND | ND | ND |
| rPA$_{form}$-CHO/AH-Gly$_3$-γDPGA$_{10}$-N | 29 | 1:0.45 | ND | ND | ND | ND |
| BSA-SL-AH/CHO-Gly$_3$-γDPGA$_{10}$-C | 3 | 1:0.06 | 103 | 822 | ND | ND |
| rEPA/Cys-γDPGA$_{15}$-N | ND | ND | ND | ND | ND | ND |
| rPA$_{form}$/Cys-Gly$_3$-γDPGA$_{10}$-N | 15 | 1:0.23 | ND | ND | ND | ND |

*γDPGA from *B. anthracis* (strain A34), 2.5 µg as a conjugate used for injection; antibodies by ELISA expressed as EU.
†Antibodies by ELISA expressed as µg Ab/ml.
‡Not applicable
§Not done
¶C or N refers to the free amino acid on the γPGA bound to the protein.

TABLE 2-continued

Dose/immunogenicity relation of conjugates prepared
with 20-mers of γDPGA bound to rPA or rEPA.

| Conjugate | Mol γDPGA/ mol protein | Protein/ γDPGA (wt/wt) | Dose/ mice (µg γDPGA) | Anti- γDPGA $3^{rd}$ injection |
|---|---|---|---|---|
| rEPA-SH/Gly$_3$-γDPGA$_{20}$-C | 6 | 1:0.23 | 2.5 | 1956 |
| | | | 5 | 2393 |
| | | | 10 | 2639 |
| | | | 20 | 2834 |

Five- to six-week old NIH general purpose mice (n = 10) injected s.c. with 0.1 ml of the conjugates two weeks apart and exsanguinated seven days after the third injection. IgG anti-γDPGA was measured by ELISA and the results expressed as the geometric mean (9,152 vs. 3,487, P = 0.003; 9,152 vs. 4,901, P = 0.04; 9,152 vs. 1,956, P < 0.0001; 7,070 vs. 2,393, P < 0.0001).

The relationship between γDPGA conjugate dosage and immunogenicity was further examined using a γDPGA-rPA conjugate (rPA/Cys-Gly$_3$-γDPGA$_{10}$-N, with 22 chains per carrier protein) at doses ranging from 2.5 µg to 0.31 µg per mouse (with 20 µg per mouse for comparison). The optimal response to γDPGA was at 1.25 µg per mouse (Table 3). The response to rPA increased with a higher immunizing dose (Table 3).

TABLE 3

Dose/immunogenicity relation of conjugate prepared
with 10-mer of γDPGA bound to rPA.

| Dose | Anti- γDPGA | | Anti-rPA | |
|---|---|---|---|---|
| µg/mouse | $2^{nd}$ injection | $3^{rd}$ injection | $2^{nd}$ injection | $3^{rd}$ injection |
| 20 | — | 3716 | — | 437 |
| 2.5 | 2231 | 5812 | 2 | 206 |
| 1.25 | 2314 | 6241 | 2 | 118 |
| 0.63 | 984 | 4943 | 0.6 | 37 |
| 0.31 | 493 | 3480 | 0.3 | 9 |

The effect of adjuvant on immunogenicity was studied using two γDPGA-rPA conjugates. Injection of the conjugate with aluminum hydroxide improved significantly the immune response to rPA (Table 4). The anti-γDPGA levels were not statistically different (Table 4).

TABLE 4

Formulation effect.

| | | Anti- γDPGA | | Anti-rPA | |
|---|---|---|---|---|---|
| Conjugate | Dose µg/mouse | $2^{nd}$ in- jection | $3^{rd}$ in- jection | $2^{nd}$ in- jection | $3^{rd}$ in- jection |
| rPA/Cys-Gly$_3$- γDPGA$_{10}$-N | 2.5 | 2231 | 5812 | 2 | 206 |
| | 2.5 + al* | 3527 | 6231 | 80 | 282 |
| rPA/Cys-Gly$_3$- γDPGA$_{10}$-C | 2.5 | 1041 | 2315 | 1 | 185 |
| | 1 | — | 2880 | — | 61 |
| | 1 + form** | — | 2556 | — | 23 |
| | 1 + al | — | 3975 | — | 258 |
| | 1 + form/al | — | 3268 | — | 297 |

*aluminum hydroxide (Alhydrogel)
**formaldehyde treatment (Porro et al., J. Infect. Dis. 142: 716–24, 1980; Nencioni et al., Infect. Immun. 59: 625–30, 1991).

Example 3

Serum IgG Anti-Carrier Protein Antibodies

This example demonstrates that conjugates of *B. anthracis* γDPGA elicited IgG anti-carrier protein antibodies in addition to anti-γDPGA antibodies.

With few exceptions, both the length and number of γDPGA chains per carrier protein were related to the level of IgG anti-carrier protein antibodies (Table 1). Conjugates prepared with γDPGA polypeptides containing 20 residues elicited low levels of carrier protein antibodies (Table 1). Conjugates prepared with either 5 or 10 glutamic acid residues per chain, and conjugates with ≦15 chains per carrier protein elicited the highest levels of IgG carrier protein antibodies (Table 1).

Example 4

Opsonophagocytic Activity of Mouse Antisera

This example demonstrates that IgG anti-DPGA antibodies have opsonophagocytic activity.

Sera from normal mice or those immunized with rEPA or rPA did not have opsonophagocytic activity. However, in mice immunized with BSA-SH/Gly$_3$-γDPGA$_{10}$-C or BSA-SH/Gly$_3$-γDPGA$_{10}$-C there was a correlation between the level of IgG anti-γDPGA antibodies and opsonophagocytosis (r=0.7, P=0.03, Table 5). Addition of γDPGA from *B. anthracis* to the immune sera showed a dose-related reduction of the opsonophagocytic titer of approximately 60%.

TABLE 5

Opsonophagocytic activity and IgG anti-γDPGA antibodies
(ELISA) elicited by BSA-SH/Gly$_3$-γDPGA$_{10}$-C.

| Sera | IgG anti-γDPGA | Reciprocal opsonophagocytic titer |
|---|---|---|
| 1196G | 407 | Not detected |
| 1195C | 1,147 | 640 |
| 1197B | 3,975 | 2,560 |
| 1190H | 3,330 | 2,560 |
| 1194D | 3,278 | 2,560 |
| 1193B | 3,178 | 2,560 |
| 1194G | 3,277 | 2,560 |
| 1191J | 5,191 | 5,120 |

Correlation coefficient between ELISA and reciprocal opsonophagocytic titer is 0.7, P = 0.03.

Example 5

Methods for Preparing Peptide and Protein Mimetics

This example describes methods for preparing peptide and protein mimetics modified at the N-terminal amino group, the C-terminal carboxyl group, and/or changing one or more of the amido linkages in the peptide to a non-amido linkage. It is understood that two or more such modifications can be coupled in one peptide or protein mimetic structure (for example, modification at the C-terminal carboxyl group and inclusion of a —CH2-carbamate linkage between two amino acids in the peptide).

For N-terminal modifications, peptides typically are synthesized as the free acid but, as noted above, can be readily prepared as the amide or ester. One can also modify the amino and/or carboxy terminus of peptide compounds to produce other compounds useful within the disclosure. Amino terminus modifications include methylating (that is, —NHCH3 or —NH(CH3)2), acetylating, adding a carbobenzoyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints. Amino terminus modifications are as recited above and include alkylating, acetylating, adding a carbobenzoyl group, forming a succinimide group, and the like. The N-terminal amino group can then be reacted as follows: (A) to form an amide group of the formula RC(O)NH— where R is as defined above by reaction with an acid halide (for example, RC(O)Cl) or acid anhydride. Typically, the reaction can be conducted by contacting about equimolar or excess amounts (for example, about 5 equivalents) of an acid halide to the peptide in an inert diluent (for example, dichloromethane) preferably containing an excess (for example, about 10 equivalents) of a tertiary amine, such as diisopropylethylamine, to scavenge the acid generated during reaction. Reaction conditions are otherwise conventional (for example, room temperature for 30 minutes). Alkylation of the terminal amino to provide for a lower alkyl N-substitution followed by reaction with an acid halide as described above will provide for N-alkyl amide group of the formula RC(O)NR—. (B) to form a succinimide group by reaction with succinic anhydride. As before, an approximately equimolar amount or an excess of succinic anhydride (for example, about 5 equivalents) can be employed and the amino group is converted to the succinimide by methods well known in the art including the use of an excess (for example, ten equivalents) of a tertiary amine such as diisopropylethylamine in a suitable inert solvent (for example, dichloromethane) (see, for example, U.S. Pat. No. 4,612,132). It is understood that the succinic group can be substituted with, for example, C2-C6 alkyl or —SR substituents that are prepared in a conventional manner to provide for substituted succinimide at the N-terminus of the peptide. Such alkyl substituents are prepared by reaction of a lower olefin (C2-C6) with maleic anhydride in the manner described by Wollenberg et al. (U.S. Pat. No. 4,612,132) and —SR substituents are prepared by reaction of RSH with maleic anhydride where R is as defined above. (C) to form a benzyloxycarbonyl-NH— or a substituted benzyloxycarbonyl-NH— group by reaction with approximately an equivalent amount or an excess of CBZ-Cl (that is, benzyloxycarbonyl chloride) or a substituted CBZ-Cl in a suitable inert diluent (for example, dichloromethane) preferably containing a tertiary amine to scavenge the acid generated during the reaction. (D) to form a sulfonamide group by reaction with an equivalent amount or an excess (for example, 5 equivalents) of R—S(O)2Cl in a suitable inert diluent dichloromethane) to convert the terminal amine into a sulfonamide where R is as defined above. Preferably, the inert diluent contains excess tertiary amine (for example, ten equivalents) such as diisopropylethylamine, to scavenge the acid generated during reaction. Reaction conditions are otherwise conventional (for example, room temperature for 30 minutes). (E) to form a carbamate group by reaction with an equivalent amount or an excess (for example, 5 equivalents) of R—OC(O)Cl or R—OC(O)OC6H4-p-NO2 in a suitable inert diluent (for example, dichloromethane) to convert the terminal amine into a carbamate where R is as defined above. Preferably, the inert diluent contains an excess (for example, about 10 equivalents) of a tertiary amine, such as diisopropylethylamine, to scavenge any acid generated during reaction. Reaction conditions are otherwise conventional (for example, room temperature for 30 minutes). (F) to form a urea group by reaction with an equivalent amount or an excess (for example, 5 equivalents) of R—N═C═O in a suitable inert diluent (for example, dichloromethane) to convert the terminal amine into a urea (that is, RNHC(O)NH—) group where R is as defined above. Preferably, the inert diluent contains an excess (for example, about 10 equivalents) of a tertiary amine, such as diisopropylethylamine. Reaction conditions are otherwise conventional (for example, room temperature for about 30 minutes).

In preparing peptide mimetics wherein the C-terminal carboxyl group is replaced by an ester (that is, —C(O)OR where R is as defined above), resins as used to prepare peptide acids are typically employed, and the side chain protected peptide is cleaved with base and the appropriate alcohol, for example, methanol. Side chain protecting groups are then removed in the usual fashion by treatment with hydrogen fluoride to obtain the desired ester.

In preparing peptide mimetics wherein the C-terminal carboxyl group is replaced by the amide —C(O)NR3R4, a benzhydrylamine resin is used as the solid support for peptide synthesis. Upon completion of the synthesis, hydrogen fluoride treatment to release the peptide from the support results directly in the free peptide amide (that is, the C-terminus is —C(O)NH2). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (that is, the C-terminus is —C(O)NRR1 where R and R1 are as defined above). Side chain protection is then removed in the usual fashion by treatment with hydrogen fluoride to give the free amides, alkylamides, or dialkylamines.

In other embodiments of the disclosure, the C-terminal carboxyl group or a C-terminal ester of a biologically active peptide can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide in solution, for example, in methylene chloride (CH2Cl2), dimethyl formamide mixtures. The cyclic peptide is then formed by internal displacement of the activated ester with the N-terminal amine. Internal cyclization as opposed to polymerization can be enhanced by use of very dilute solutions. Such methods are well known in the art.

One can cyclize active peptides for use within the disclosure, or incorporate a desamino or descarboxy residue at the termini of the peptide, so that there is no terminal amino or carboxyl group, to decrease susceptibility to proteases, or to restrict the conformation of the peptide. C-terminal functional groups among peptide analogs and mimetics of the present disclosure include amide, amide lower alkyl, amide di(lower alkyl), lower alkoxy, hydroxy, and carboxy, and the lower ester derivatives thereof, and the pharmaceutically acceptable salts thereof.

Other methods for making peptide and protein derivatives and mimetics for use within the methods and compositions of the disclosure are described in Hruby et al., (*Biochem. J.* 268:249-62, 1990). According to these methods, biologically active peptides and proteins serve as structural models for non-peptide mimetic compounds having similar biological activity as the native peptide or protein. Those of skill in the art recognize that a variety of techniques are available for constructing compounds with the same or similar desired biological activity as the lead peptide or protein compound, or that have more favorable activity than the lead with respect a desired property such as solubility, stability, and susceptibility to hydrolysis and proteolysis (see, for example, Morgan and Gainor, *Ann. Rep. Med. Chem.* 24:243-52, 1989). These techniques include, for example, replacing a peptide backbone with a backbone composed of phosphonates, amidates, carbamates, sulfonamides, secondary amines, and/or N-methylamino acids.

Peptide and protein mimetics wherein one or more of the peptidyl linkages (—C(O)NH—) have been replaced by such linkages as a —CH2-carbamate linkage, a phosphonate linkage, a —CH2-sulfonamide linkage, a urea linkage, a secondary amine (—CH2NH—) linkage, and an alkylated peptidyl linkage (—C(O)NR6- where R6 is lower alkyl) are prepared, for example, during conventional peptide synthesis by merely substituting a suitably protected amino acid analogue for the amino acid reagent at the appropriate point during synthesis. Suitable reagents include, for example, amino acid analogues wherein the carboxyl group of the amino acid has been replaced with a moiety suitable for forming one of the above linkages. For example, if one desires to replace a —C(O)NR— linkage in the peptide with a —CH2-carbamate linkage (—CH2OC(O)NR—), then the carboxyl (—COOH) group of a suitably protected amino acid is first reduced to the —CH2OH group which is then converted by conventional methods to a —OC(O)Cl functionality or a para-nitrocarbonate —OC(O)O—C6H4-p-NO2 functionality. Reaction of either of such functional groups with the free amine or an alkylated amine on the N-terminus of the partially fabricated peptide found on the solid support leads to the formation of a —CH2OC(O)NR— linkage. For a more detailed description of the formation of such —CH2-carbamate linkages, see, for example, Cho et al., *Science* 261:1303-05, 1993.

Replacement of an amido linkage in an active peptide with a —CH2-sulfonamide linkage can be achieved by reducing the carboxyl (—COOH) group of a suitably protected amino acid to the —CH2OH group, and the hydroxyl group is then converted to a suitable leaving group such as a tosyl group by conventional methods. Reaction of the derivative with, for example, thioacetic acid followed by hydrolysis and oxidative chlorination will provide for the —CH2-S(O)2Cl functional group which replaces the carboxyl group of the otherwise suitably protected amino acid. Use of this suitably protected amino acid analogue in peptide synthesis provides for inclusion of an —CH2S(O)2NR— linkage that replaces the amido linkage in the peptide thereby providing a peptide mimetic. For a more complete description on the conversion of the carboxyl group of the amino acid to a —CH2S(O)2Cl group, see, for example, Weinstein and Boris, *Chemistry & Biochemistry of Amino Acids, Peptides and Proteins*, Vol. 7, pp. 267-357, Marcel Dekker, Inc., New York, 1983. Replacement of an amido linkage in an active peptide with a urea linkage can be achieved, for example, in the manner set forth in U.S. patent application Ser. No. 08/147,805.

Secondary amine linkages wherein a —CH2NH— linkage replaces the amido linkage in the peptide can be prepared by employing, for example, a suitably protected dipeptide analogue wherein the carbonyl bond of the amindo linkage has been reduced to a CH2 group by conventional methods. For example, in the case of diglycine, reduction of the amide to the amine will yield after deprotection H2NCH2CH2NHCH2 COOH that is then used in N-protected form in the next coupling reaction. The preparation of such analogues by reduction of the carbonyl group of the amido linkage in the dipeptide is well known in the art.

The biologically active peptide and protein agents of the present disclosure can exist in a monomeric form with no disulfide bond formed with the thiol groups of cysteine residue(s) that may be present in the subject peptide or protein. Alternatively, an intermolecular disulfide bond between thiol groups of cysteines on two or more peptides or proteins can be produced to yield a multimeric (for example, dimeric, tetrameric or higher oligomeric) compound. Certain of such peptides and proteins can be cyclized or dimerized via displacement of the leaving group by the sulfur of a cysteine or homocysteine residue (see, for example, Barker et al., *J. Med. Chem.* 35:2040-48, 1992 and Or et al., *J. Org. Chem.* 56:3146-49, 1991). Thus, one or more native cysteine residues can be substituted with a homocysteine. Intramolecular or intermolecular disulfide derivatives of active peptides and proteins provide analogs in which one of the sulfurs has been replaced by a CH2 group or other isostere for sulfur. These analogs can be made via an intramolecular or intermolecular displacement, using methods known in the art.

Example 6

Delivery of γPGA Conjugates

This example demonstrates that delivery of γPGA conjugates can be enhanced by methods and agents that target selective transport mechanisms and promote endo- or transcytocis of macromoloecular drugs.

In this regard, the compositions and delivery methods of the disclosure optionally incorporate a selective transport-enhancing agent that facilitates transport of one or more biologically active agents. These transport-enhancing agents can be employed in a combinatorial formulation or coordinate administration protocol with one or more of the peptides, proteins, analogs and mimetics disclosed herein, to coordinately enhance delivery of the biologically active agent(s) into target cells. Exemplary selective transport-enhancing agents for use within this aspect of the disclosure include, but are not limited to, glycosides, sugar-containing molecules, and binding agents such as lectin binding agents, which are known to interact specifically with epithelial transport barrier components (see, for example, Goldstein et al., *Annu. Rev. Cell. Biol.* 1:1-39, 1985). For example, specific "bioadhesive" ligands, including various plant and bacterial lectins, which bind to cell surface sugar moieties by receptor-mediated interactions can be employed as carriers or conjugated transport mediators for enhancing delivery of γPGA conjugates within the disclosure. Certain bioadhesive ligands for use within the disclosure will mediate transmission of biological signals to epithelial target cells that trigger selective uptake of the adhesive ligand by specialized cellular transport processes (endocytosis or transcytosis). These transport mediators can therefore be employed as a "carrier system" to stimulate or direct selective uptake of a γPGA conjugate within the methods of the disclosure. To utilize these transport-enhancing agents, general carrier formulation and/or conjugation methods known in the art are used to complex or otherwise coordinately administer a selective transport enhancer (for example, a receptor-specific ligand) and a γPGA conjugate to trigger or mediate enhanced endo- or transcytosis of the γPGA conjugate into specific target cell(s), tissue(s) or compartment(s).

Lectins are plant proteins that bind to specific sugars found on the surface of glycoproteins and glycolipids of eukaryotic cells. Concentrated solutions of lectins have a "mucotractive" effect, and various studies have demonstrated rapid receptor mediated endocytosis of lectins and lectin conjugates (for example, concanavalin A conjugated with colloidal gold particles) across mucosal surfaces. Additional studies have reported that the uptake mechanisms for lectins can be utilized for intestinal drug targeting in vivo. In certain of these studies, polystyrene nanoparticles (500 nm) were covalently coupled to tomato lectin and reported yielded improved systemic uptake after oral administration to rats. In addition to plant lectins, microbial adhesion and invasion factors provide a rich source of candidates for use as adhesive/selective transport carriers within the compositions and methods of the disclosure (see, for example, Lehr, *Crit. Rev. Therap. Drug Carrier Syst.* 11:177-218, 1995 and Swann, *Pharmaceutical Research* 15:826-32, 1998). Two components are necessary for bacterial adherence processes, a bacterial "adhesin" (adherence or colonization factor) and a receptor on the host cell surface. Bacteria causing mucosal infections need to penetrate the mucus layer before attaching themselves to the epithelial surface. This attachment is usually mediated by bacterial fimbriae or pilus structures, although other cell surface components can also take part in the process. Adherent bacteria colonize mucosal epithelia by multiplication and initiation of a series of biochemical reactions inside the target cell through signal transduction mechanisms (with or without the help of toxins).

Associated with these invasive mechanisms, a wide diversity of bioadhesive proteins (for example, invasin, internalin) originally produced by various bacteria and viruses are known. These allow for extracellular attachment of such microorganisms with an impressive selectivity for host species and even particular target tissues. Signals transmitted by such receptor-ligand interactions trigger the transport of intact, living microorganisms into, and eventually through, epithelial cells by endo- and transcytotic processes. Such naturally occurring phenomena can be harnessed (for example, by complexing a γPGA conjugate with an adhesin) according to the teachings herein for enhanced delivery of γPGA conjugates and/or other biologically active compounds. One advantage of this strategy is that the selective carrier partners thus employed are substrate-specific, leaving the natural barrier function of epithelial tissues intact against other solutes (see, for example, Lehr, *Drug Absorption Enhancement*, pp. 325-362, de Boer, Ed., Harwood Academic Publishers, 1994).

Various bacterial and plant toxins that bind epithelial surfaces in a specific, lectin-like manner are also useful within the methods and compositions of the disclosure. For example, diphtheria toxin enters host cells rapidly by receptor mediated endocytosis. Likewise, the B subunit of the *E. coli* heat labile toxin binds to the brush border of intestinal epithelial cells in a highly specific, lectin-like manner. Uptake of this toxin and transcytosis to the basolateral side of the enterocytes has been reported in vivo and in vitro. Other researches have expressed the transmembrane domain of diphtheria toxin in *E. coli* as a maltose-binding fusion protein and coupled it chemically to high-Mw poly-L-lysine. The resulting complex was successfully used to mediate internalization of a reporter gene in vitro. In addition to these examples, *Staphylococcus aureus* produces a set of proteins (for example, staphylococcal enterotoxin A, staphylococcal enterotoxin B and toxic shock syndrome toxin 1) which act both as superantigens and toxins. Studies relating to these proteins have reported dose-dependent, facilitated transcytosis of staphylococcal enterotoxin B and toxic shock syndrome toxin 1 in Caco-2 cells.

Various plant toxins, mostly ribosome-inactivating proteins, have been identified that bind to any mammalian cell surface expressing galactose units and are subsequently internalized by receptor mediated endocytosis. Toxins such as nigrin b, sarcin, ricin and saporin, viscumin, and modeccin are highly toxic upon oral administration (that is, they are rapidly internalized). Therefore, modified, less toxic subunits of these compound will be useful within the disclosure to facilitate the uptake of γPGA conjugates and other biologically active agents, including PA, other bacterial products and analogs, variants, derivatives and mimetics thereof.

Viral hemagglutinins include another type of transport agent to facilitate delivery of γPGA conjugates and other biologically active agents within the methods and compositions of the disclosure. The initial step in many viral infections is the binding of surface proteins (hemagglutinins) to mucosal cells. These binding proteins have been identified for most viruses, including rotaviruses, *Varicella zoster* virus, semliki forest virus, adenoviruses, potato leafroll virus, and reovirus. These and other exemplary viral hemagglutinins can be employed in a combinatorial formulation (for example, a mixture or conjugate formulation) or coordinate administration protocol with, for example, one or more γPGA conjugates, PA immunogens, other bacterial products, or analogs, variants, derivatives and mimetics thereof. Alternatively, viral hemagglutinins can be employed in a combinatorial formulation or coordinate administration protocol to directly enhance delivery of a γPGA conjugate or other biologically active agent within the disclosure.

A variety of endogenous, selective transport-mediating factors are also available for use within the disclosure. Exemplary among these are protocytotic transport carriers within the folate carrier system, which mediate transport of the vitamin folic acid into target cells via specific binding to the folate receptor (see, for example, Reddy et al., *Crit. Rev. Ther. Drug Car. Syst.* 15:587-27, 1998). This receptor system has been used in drug-targeting approaches to cancer cells, but also in protein delivery, gene delivery, and targeting of antisense oligonucleotides to a variety of cell types. Folate-drug conjugates are well suited for use within the methods and compositions of the disclosure, because they allow penetration of target cells exclusively via folate receptor-mediated endocytosis. When folic acid is covalently linked to a biologically active agent, folate receptor binding affinity (KD~10-10M) is not significantly compromised, and endocytosis proceeds relatively unhindered, promoting uptake of the attached active agent by the folate receptor-expressing cell.

In addition to the folate receptor pathway, a variety of additional methods to stimulate transcytosis within the disclosure are directed to the transferrin receptor pathway, and the riboflavin receptor pathway. In one aspect, conjugation of a PGA conjugate or other biologically active agent to riboflavin can effectuate receptor mediated endocytosis uptake. Yet additional embodiments of the disclosure utilize vitamin B12 (cobalamin) as a specialized transport protein (for example, conjugation partner) to facilitate entry of γPGA conjugates and other biologically active agents into target cells. Certain studies suggest that this particular system can be employed for mucosal delivery into the intestine. Still other embodiments of the disclosure utilize transferrin as a carrier or stimulant of receptor mediated endocytosis of mucosally delivered biologically active agents. Transferrin, an 80 kDa iron-transporting glycoprotein, is efficiently taken up into cells by receptor mediated endocytosis. Transferrin receptors are found on the surface of most proliferating cells, in elevated numbers on erythroblasts and on many kinds of tumors. Each of the foregoing agents that stimulate receptor-mediated transport can be employed within the methods of the disclosure as combinatorially formulated (for example, conjugated) and/or coordinately administered agents to enhance receptor-mediated transport of γPGA conjugates and other biologically active agents, including, PA, carriers, linkers, and other bacterial toxins and analogs, variants, derivatives and mimetics thereof.

Immunoglobulin transport mechanisms provide yet additional endogenous pathways and reagents for enhancing delivery of γPGA conjugates and other active agents within the methods and compositions of the disclosure. Receptor-mediated transcytosis of immunoglobulin G (IgG) across the neonatal small intestine serves to convey passive immunity to many newborn mammals. Within the methods and compositions of the present disclosure, IgG and other immune system-related carriers (including polyclonal and monoclonal antibodies and various fragments thereof) can be complexed or otherwise coordinately administered with γPGA conjugates and other biologically active agents to provide for targeted delivery, typically by receptor-mediated transport. For example, the γPGA conjugate or other biologically active agent can be covalently linked to the IgG or other immunological active agent or, alternatively, formulated in liposomes or other carrier vehicle which is in turn modified (for example, coated or covalently linked) to incorporate IgG or other immunological transport enhancer. In certain embodiments, polymeric IgA and/or IgM transport agents are employed, which bind to the polymeric immunoglobulin receptors of target epithelial cells. Within these methods, expression of polymeric immunoglobulin receptors can be enhanced by cytokines.

Within more detailed aspects of the disclosure, antibodies and other immunological transport agents can be themselves modified for enhanced delivery of γPGA conjugates or other biologically active agents. For example, antibodies can be more effectively administered within the methods and compositions of the disclosure by charge modifying techniques. In one such aspect, an antibody drug delivery strategy involving antibody cationization is utilized that facilitates both trans-endothelial migration and target cell endocytosis (see, for example, Pardridge, et al., *JPET* 286:548-44, 1998). In one such strategy, the pI of the antibody is increased by converting surface carboxyl groups of the protein to extended primary amino groups. These cationized homologous proteins have no measurable tissue toxicity and have minimal immunogenicity. In addition, monoclonal antibodies can be cationized with retention of affinity for the target protein.

Additional selective transport-enhancing agents for use within the disclosure include whole bacteria and viruses, including genetically engineered bacteria and viruses, as well as components of such bacteria and viruses. This aspect of the disclosure includes the use of bacterial ghosts and subunit constructs, for example, as described by Huter et al., *J. Control. Rel.* 61:51-63, 1999. Bacterial ghosts are non-denatured bacterial cell envelopes, for example as produced by the controlled expression of the plasmid-encoded lysis gene E of bacteriophage PhiX174 in gram-negative bacteria. Protein E-specific lysis does not cause any physical or chemical denaturation to bacterial surface structures, and bacterial ghosts are therefore useful in development of inactivated whole-cell vaccines. Ghosts produced from *Actinobacillus pleuropneumoniae, Pasteurella haemolytica* and *Salmonella* sp. have proved successful in vaccination experiments. Recombinant bacterial ghosts can be created by the expression of foreign genes fused to a membrane-targeting sequence, and thus can carry foreign therapeutic peptides and proteins anchored in their envelope. The fact that bacterial ghosts preserve a native cell wall, including bioadhesive structures like fimbriae of their living counterparts, makes them suitable for the attachment to specific target tissues such as mucosal surfaces. Bacterial ghosts have been shown to be readily taken up by macrophages, thus adhesion of ghosts to specific tissues can be followed by uptake through phagocytes.

In view of the foregoing, a wide variety of ligands involved in receptor-mediated transport mechanisms are known in the art and can be variously employed within the methods and compositions of the disclosure (for example, as conjugate partners or coordinately administered delivery enhancers) to enhance delivery or receptor-mediated transport of γPGA conjugates and other biologically active agents, including PA or other bacterial products. Generally, these ligands include hormones and growth factors, bacterial adhesins and toxins, lectins, metal ions and their carriers, vitamins, immunoglobulins, whole viruses and bacteria or selected components thereof. Exemplary ligands among these classes include, for example, calcitonin, prolactin, epidermal growth factor, glucagon, growth hormone, estrogen, lutenizing hormone, platelet derived growth factor, thyroid stimulating hormone, thyroid hormone, cholera toxin, diphtheria toxin, *E. coli* heat labile toxin, Staphylococcal enterotoxins A and B, ricin, saporin, modeccin, nigrin, sarcin, concanavalin A, transcobalantin, catecholamines, transferrin, folate, riboflavin, vitamin B1, low density lipoprotein, maternal IgO, polymeric IgA, adenovirus, vesicular stomatitis virus, Rous sarcoma virus, *V. cholerae, Kiebsiella* strains, *Serratia* strains, parainfluenza virus, respiratory syncytial virus, *Varicella zoster*, and *Enterobacter* strains (see, for example, Swann, *Pharmaceutical Research* 15:826-32, 1998).

In certain additional embodiments of the disclosure, membrane-permeable peptides (for example, "arginine rich peptides") are employed to facilitate delivery of γPGA conjugates or other biologically active agents of the disclosure. While the mechanism of action of these peptides remains to be fully elucidated, they provide useful delivery enhancing adjuncts for use within the compositions and methods herein. In one example, a basic peptide derived from human immunodeficiency virus (HIV)-1 Tat protein (for example, residues 48-60) facilitates translocation through cell membranes and can be utilized for enhancing delivery of exogenous proteins and peptides into cells. The sequence of Tat (GRKKRRQRRRPPQ, SEQ ID NO: 1) includes a highly basic and hydrophilic peptide, which contains 6 arginine and 2 lysine residues in its 13 amino acid residues. Various other arginine-rich peptides have been identified which have a translocation activity similar to Tat-(48-60). These include such peptides as the D-amino acid- and arginine-substituted Tat-(48-60), the RNA-binding peptides derived from virus proteins, such as HIV-1 Rev, and flock house virus coat proteins, and the DNA binding segments of leucine zipper proteins, such as cancer-related proteins c-Fos and c-Jun, and the yeast transcription factor GCN4 (see, for example, Futaki et al., *J. Biol. Chem.* 276:5836-40, 2000).

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the claims below.

We claim:

1. An immunogenic conjugate comprising a synthetic homopolymer of poly-γ-glutamic acid (γPGA) polypeptide covalently linked to a carrier, wherein the conjugate elicits an immune response against poly-γ-glutamic acid (γPGA) polypeptide in a subject.

2. The conjugate of claim 1, wherein the synthetic homopolymer of γPGA polypeptide comprises 5-20 glutamic acid residues.

3. The conjugate of claim 1, wherein the synthetic homopolymer of γPGA polypeptide comprises 10-15 glutamic acid residues.

4. The conjugate of claim 1, wherein the synthetic homopolymer of γPGA polypeptide is a decameric γPGA polypeptide.

5. The conjugate of claim 1, wherein the carrier is selected from the group consisting of: (a) recombinant B. anthracis protective antigen, (b) recombinant P. aeruginosa exotoxin A, (c) tetanus toxoid, (d) diphtheria toxoid, (e) pertussis toxoid, (f) C. perfringens toxoid, (g) hepatitis B surface antigen, (h) hepatitis B core antigen, (i) keyhole limpet hemocyanin, (j) horseshoe crab hemocyanin, (k) edestin, (l) mammalian serum albumins, (m) mammalian immunoglobulins, and (n) combinations of two or more thereof.

6. The conjugate of claim 1, wherein the carrier comprises recombinant B. anthracis protective antigen.

7. The conjugate of claim 1, wherein the synthetic homopolymer of poly-γ-glutamic acid (γPGA) polypeptide is the D-conformation, the L-conformation, or a mixture of the D-conformation and the L-conformation.

8. The conjugate of claim 1, wherein the synthetic homopolymer of poly-γ-glutamic acid (γPGA) polypeptide is a γDPGA polypeptide.

9. The conjugate of claim 1, wherein the synthetic homopolymer of poly-γ-glutamic acid (γPGA) polypeptide is a decameric γDPGA polypeptide and the carrier comprises recombinant *B. anthracis* protective antigen.

10. The conjugate of claim 1, wherein the carrier is covalently linked to either the amino or carboxyl terminus of the synthetic homopolymer of poly-γ-glutamic acid (γPGA) polypeptide.

11. The conjugate of claim 1, wherein the carrier is covalently linked to the synthetic homopolymer of poly-γ-glutamic acid (γPGA) polypeptide via a thioether, disulfide, or amide bond.

12. The conjugate of claim 1, wherein the density of the synthetic homopolymer of poly-γ-glutamic acid (γPGA) polypeptide to carrier is between about 5:1 and about 32:1.

13. The conjugate of claim 1, wherein the density of the synthetic homopolymer of poly-γ-glutamic acid (γPGA) polypeptide to carrier is between about 10:1 and about 15:1.

14. The conjugate of claim 1, wherein the synthetic homopolymer of γPGA polypeptide is covalently linked to the carrier via an aldehyde (CHO)/adipic acid hydrazide (AH) linkage.

15. A composition comprising the conjugate of claim 1 and a pharmaceutically acceptable vehicle.

16. The composition of claim 15, further comprising an adjuvant.

17. A composition comprising the conjugate of claim 8 and a pharmaceutically acceptable vehicle.

18. The composition of claim 17, further comprising an adjuvant.

19. A method of eliciting an immune response against a *Bacillus* antigenic epitope in a subject, comprising introducing into the subject the composition of claim 15, thereby eliciting an immune response in the subject.

20. The conjugate of claim 1, wherein the carrier is a polysaccharide or a polypeptide.

21. The conjugate of claim 1, wherein the carrier is a bacterial toxin or a viral protein.

22. The conjugate of claim 5, wherein the carrier is selected from the group consisting of (a) recombinant *B. anthracis* protective antigen, (b) recombinant *P. aeruginosa* exotoxin A, (c) tetanus toxoid, (d) diphtheria toxoid, (e) pertussis toxoid, (f) *C. perfringens* toxoid, (g) hepatitis B surface antigen, and (h) hepatitis B core antigen.

23. The conjugate of claim 8, wherein the carrier is *B. anthracis* protective antigen, and the conjugate elicits an immune response against γDPGA and against *B. anthracis* protective antigen.

24. The conjugate of claim 1, wherein the conjugate includes a plurality of synthetic homopolymer of γPGA polypeptide chains per carrier molecule.

25. The conjugate of claim 1, wherein the conjugate has a density of synthetic homopolymer of γPGA chains to carrier molecule of at least about 5:1.

26. The conjugate of claim 24, wherein the carrier is a polymeric carrier.

27. The conjugate of claim 25, wherein the carrier is a polymeric carrier.

28. An immunogenic conjugate comprising a *Bacillus* poly-γ-glutamic acid (γPGA) polypeptide covalently linked to a carrier, wherein the carrier is selected from the group consisting of: (a) recombinant *B. anthracis* protective antigen, (b) recombinant *P. aeruginosa* exotoxin A, (c) tetanus toxoid, (d) diphtheria toxoid, (e) pertussis toxoid, (f) *C. perfringens* toxoid, (g) hepatitis B surface antigen, (h) hepatitis B core antigen, (i) keyhole limpet hemocyanin, (j) horseshoe crab hemocyanin, (k) edestin, (l) mammalian serum albumins, and (m) combinations thereof, and wherein the conjugate elicits an immune response against *Bacillus* poly-γ-glutamic acid (γPGA) polypeptide in a subject.

29. The conjugate of claim 28, wherein the carrier comprises recombinant *B. anthracis* protective antigen.

30. The conjugate of claim 28, wherein the *Bacillus* γPGA polypeptide comprises a *B. anthracis*, *B. licheniformis*, *B. pumilus*, or *B. subtilis* γPGA polypeptide.

31. The conjugate of claim 28, wherein the *Bacillus* γPGA polypeptide is the D-conformation, the L-conformation, or a mixture of the D-conformation and the L-conformation.

32. The conjugate of claim 28, wherein the *Bacillus* γPGA polypeptide is a *B. anthracis* capsular γDPGA polypeptide.

33. The conjugate of claim 28, wherein the carrier is covalently linked to either the amino or carboxyl terminus of the *Bacillus* γPGA polypeptide.

34. The conjugate of claim 28, wherein the carrier is covalently linked to the *Bacillus* γPGA polypeptide via a thioether, disulfide, or amide bond.

35. The conjugate of claim 28, wherein the *Bacillus* γPGA polypeptide is covalently linked to the carrier via an aldehyde (CHO)/adipic acid hydrazide (AH) linkage.

36. A composition comprising the conjugate of claim 28 and a pharmaceutically acceptable vehicle.

37. The composition of claim 36, further comprising an adjuvant.

38. A method of eliciting an immune response against a *Bacillus* antigenic epitope in a subject, comprising introducing into the subject the composition of claim 36, thereby eliciting an immune response in the subject.

39. The conjugate of claim 28, wherein the carrier is selected from the group consisting of (a) recombinant *B. anthracis* protective antigen, (b) recombinant *P. aeruginosa* exotoxin A, (c) tetanus toxoid, (d) diphtheria toxoid, (e) pertussis toxoid, (f) *C. perfringens* toxoid, (g) hepatitis B surface antigen, and (h) hepatitis B core antigen.

40. The conjugate of claim 28, wherein the conjugate includes a plurality of *Bacillus* γPGA polypeptide chains per carrier molecule.

41. The conjugate of claim 28, wherein the conjugate has a density of *Bacillus* γPGA chains to carrier molecule of at least about 5:1.

42. An immunogenic conjugate comprising poly-γ-glutamic acid (γPGA) covalently linked to a carrier, wherein the conjugate elicits an immune response against poly-γ-glutamic acid (γPGA) in a subject, and the conjugate has a density of γPGA chains to carrier molecule of at least about 5:1.

* * * * *

UNITED STATES PATENT AND TRADEMARK OFFICE
CERTIFICATE OF CORRECTION

PATENT NO. : 7,803,386 B2
APPLICATION NO. : 10/559825
DATED : September 28, 2010
INVENTOR(S) : Rachel Schneerson et al.

It is certified that error appears in the above-identified patent and that said Letters Patent is hereby corrected as shown below:

In the Specification:

Column 1, line 48, "(Welkos eta.," should read --(Welkos et al.,--.

Column 1, line 65, "herein The" should read --herein. The--.

Column 5, line 26, "*B. lentinorbus*," should read --*B. lentimorbus*,--.

Column 5, line 27, "*B. macquarienis*," should read --*B. macquariensis*,--.

Column 7, line 10, "response for example," should read --response, for example,--.

Column 7, line 42, "Inhibiting the fill" should read --Inhibiting the full--.

Column 11, line 21, "subject Ideally," should read --subject. Ideally,--.

Column 12, line 13, "art suitable" should read --art. Suitable--.

Column 13, line 42, "which nay be" should read --which may be--.

Column 14, line 55, "*B. anthracis.* PA" should read --*B. anthracis* PA--.

Column 15, line 41, "lower alkyl amide di(lower alkyl)," should read --lower alkyl, amide di(lower alkyl),--.

Column 19, line 6, "agent Desired" should read --agent. Desired--.

Column 23, line 5, "ice vitro" should read --in vitro--.

Column 24, line 33, "*anthracis* γPGA," should read --*anthracis* γDPGA,--.

Column 28, line 17, "γ-mercaptoethanol" should read --β-mercaptoethanol--.

Column 28, lines 28-29, "30 γ-Lys-NH$_2$" should read --30 ε-Lys-NH$_2$--.

Column 37, line 2, "with respect a" should read --with respect to a--.

Column 37, line 60, "amindo linkage" should read --amido linkage--.

Column 40, line 52, "PGA conjugate" should read --γPGA conjugate--.

Signed and Sealed this
Eighth Day of October, 2013

Teresa Stanek Rea
*Deputy Director of the United States Patent and Trademark Office*